US012269867B2

(12) United States Patent
Falkenstein et al.

(10) Patent No.: US 12,269,867 B2
(45) Date of Patent: *Apr. 8, 2025

(54) RE-USE OF ENZYMES IN IN VITRO GLYCOENGINEERING OF ANTIBODIES

(71) Applicant: Hoffmann-La Roche Inc., Little Falls, NJ (US)

(72) Inventors: Roberto Falkenstein, Penzberg (DE); Sebastian Malik, Penzberg (DE); Ingrid Grunert, Penzberg (DE); Marco Thomann, Penzberg (DE); Matthias Freiherr Von Roman, Penzberg (DE); Heiko Walch, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 712 days.

This patent is subject to a terminal disclaimer.

(21) Appl. No.: 16/447,106

(22) Filed: Jun. 20, 2019

(65) Prior Publication Data

US 2020/0165321 A1 May 28, 2020

Related U.S. Application Data

(63) Continuation of application No. PCT/EP2017/083430, filed on Dec. 19, 2017.

(30) Foreign Application Priority Data

Dec. 21, 2016 (EP) .................................... 16205586
Feb. 20, 2017 (EP) .................................... 17157005

(51) Int. Cl.
*C07K 16/00* (2006.01)
*C07K 1/18* (2006.01)

(52) U.S. Cl.
CPC ............... *C07K 16/00* (2013.01); *C07K 1/18* (2013.01); *C07K 2317/21* (2013.01); *C07K 2317/24* (2013.01); *C07K 2317/31* (2013.01); *C07K 2317/35* (2013.01); *C07K 2317/41* (2013.01); *C07K 2317/55* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,202,238 A | 4/1993 | Fell et al. |
| 5,204,244 A | 4/1993 | Fell et al. |
| 5,648,237 A | 7/1997 | Carter |
| 5,731,168 A | 3/1998 | Carter et al. |
| 5,750,373 A | 5/1998 | Garrard et al. |
| 5,770,429 A | 6/1998 | Lonberg et al. |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,171,586 B1 | 1/2001 | Lam et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,982,321 B2 | 1/2006 | Winter |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,527,791 B2 | 5/2009 | Adams et al. |
| 2005/0079574 A1 | 4/2005 | Bond |
| 2005/0119455 A1 | 6/2005 | Fuh et al. |
| 2005/0260186 A1 | 11/2005 | Bookbinder et al. |
| 2005/0266000 A1 | 12/2005 | Bond |
| 2006/0025576 A1 | 2/2006 | Miller et al. |
| 2006/0057638 A1 | 3/2006 | Bosques et al. |

(Continued)

FOREIGN PATENT DOCUMENTS

| | | |
|---|---|---|
| CN | 101506238 A | 8/2009 |
| CN | 101784670 A | 7/2010 |

(Continued)

OTHER PUBLICATIONS

Finch et al (Carbohydrate Res 303: 339-345, 1997) (Year: 1997).*
Almagro et al., "Humanization of antibodies" Front Biosci 13:1619-1633 (Jan. 1, 2008).
Armour et al., "Recombinant Human IgG Molecules Lacking Fcγ Receptor I Binding and Monocyte Triggering Activities" Eur J Immunol 29(8):2613-2624 (May 10, 1999).
Ausubel et al. Current Protocols in Molecular Biology (Table of Contents only), John Wiley & Sons, Inc., vol. 1-3:Table of Contents ( 2001).
Azuma, H., et al., "A publication of reliable methods for the preparation of organic compounds" Org Synth 88:152-161 (Jan. 14, 2011).
Baca et al., "Antibody humanization using monovalent phage display" J Biol Chem 272(16):10678-10684 (Apr. 18, 1997).

(Continued)

*Primary Examiner* — Kimberly Ballard
*Assistant Examiner* — Aditi Dutt
(74) *Attorney, Agent, or Firm* — Genentech, Inc.

(57) ABSTRACT

Herein is reported a method for the enzymatic preparation/production of an antibody with a modified glycosylation in the Fc-region comprises the steps of incubating an antibody that has a glycosylation in the Fc-region with one or more enzymes for a time sufficient and under conditions suitable to modify the glycosylation of the Fc-region to a defined form, separating in one or more chromatography steps the antibody with a modified glycosylation in the Fc-region from the one or more enzymes and thereby producing the antibody with a modified glycosylation in the Fc-region and one or more recycled enzymes, and repeating the incubating step with the one or more recycled enzymes at least once.

19 Claims, 1 Drawing Sheet
Specification includes a Sequence Listing.

(56) References Cited

U.S. PATENT DOCUMENTS

| | | | |
|---|---|---|---|
| 2006/0104968 | A1 | 5/2006 | Bookbinder et al. |
| 2006/0127950 | A1 | 6/2006 | Bosques et al. |
| 2007/0061900 | A1 | 3/2007 | Murphy et al. |
| 2007/0117126 | A1 | 5/2007 | Sidhu et al. |
| 2007/0160598 | A1 | 7/2007 | Dennis et al. |
| 2007/0237764 | A1 | 10/2007 | Birtalan et al. |
| 2007/0292936 | A1 | 12/2007 | Barthelemy et al. |
| 2008/0069820 | A1 | 3/2008 | Fuh et al. |
| 2009/0002360 | A1 | 1/2009 | Chen et al. |
| 2010/0286067 | A1 | 11/2010 | DeFrees et al. |
| 2011/0263828 | A1 | 10/2011 | Wong et al. |
| 2012/0129216 | A1 | 5/2012 | Harberger et al. |
| 2020/0165320 | A1 | 5/2020 | Falkenstein et al. |

FOREIGN PATENT DOCUMENTS

| | | | |
|---|---|---|---|
| CN | 102471376 | A | 5/2012 |
| CN | 103154017 | A | 6/2013 |
| CN | 104220603 | A | 12/2014 |
| EP | 0 307 434 | B1 | 9/1993 |
| EP | 0 307 434 | B2 | 9/1993 |
| JP | 2006-520187 | | 9/2006 |
| JP | 2009-504569 | A | 2/2009 |
| JP | 2013-500002 | A | 1/2013 |
| WO | 92/16640 | A1 | 10/1992 |
| WO | 93/08829 | A1 | 5/1993 |
| WO | 98/33523 | A1 | 8/1998 |
| WO | 98/52976 | A1 | 11/1998 |
| WO | 00/34317 | A2 | 6/2000 |
| WO | 00/34317 | A3 | 6/2000 |
| WO | 2004/083862 | | 9/2004 |
| WO | 2005/012297 | A1 | 2/2005 |
| WO | 2006/029879 | A2 | 3/2006 |
| WO | 2006/044908 | A2 | 4/2006 |
| WO | 2007/005786 | A2 | 1/2007 |
| WO | 2007/131676 | A1 | 11/2007 |
| WO | 2008/011633 | A2 | 1/2008 |
| WO | 2009/027041 | A1 | 3/2009 |
| WO | 2009/080251 | A1 | 7/2009 |
| WO | 2009/080252 | A1 | 7/2009 |
| WO | 2009/080253 | A1 | 7/2009 |
| WO | 2009/080254 | A1 | 7/2009 |
| WO | 2009/089004 | A1 | 7/2009 |
| WO | 2010/112193 | A1 | 10/2010 |
| WO | 2010/115589 | A1 | 10/2010 |
| WO | 2010/136172 | A1 | 12/2010 |
| WO | 2010/145792 | A1 | 12/2010 |
| WO | 2010/145793 | A1 | 12/2010 |
| WO | 2011/012297 | A1 | 2/2011 |
| WO | 2012/016984 | A1 | 2/2012 |
| WO | 2013/088259 | A2 | 6/2013 |
| WO | 2013/120066 | A1 | 8/2013 |
| WO | 2013/158279 | A1 | 10/2013 |
| WO | 2015/123754 | A1 | 8/2015 |
| WO | 2016/037947 | | 3/2016 |
| WO | 2017/072062 | A1 | 5/2017 |

OTHER PUBLICATIONS

Boerner et al., "Production of antigen-specific human monoclonal antibodies from in vitro- primed human splenocytes" J Immunol 147(1):86-95 (Jul. 1, 1991).

Boyd et. al. et al., "The Effect of the Removal of Sialic Acid, Galactose and Total Carbohydrate on the Functional Activity of Campath-1H." Mol Immunol 32:1311-1318 ( 1995).

Brennan et al., "Preparation of bispecific antibodies by chemical recombination of monoclonal immunoglobulin G 1 fragments" Science 229(4708):81-83 (Jul. 5, 1985).

Brinkmann, U., et al., "The making of bispecific antibodies" MABS 9(2):182-212 (Jan. 10, 2017).

Brodeur, et al., "Mouse-human myeloma partners for the production of heterohybridomas" Monoclonal Antibody Production Techniques and Applications (New York: Marcel Dekker, Inc.),:51-63 ( 1987).

Brueggemann, M., et al., "Comparison of the effector functions of human immunoglobulins using a matched set of chimeric antibodies" J. Exp. Med. 166(5):1351-1361 (Nov. 1, 1987).

Brunhouse, R. et al., "Isotypes of IgG comparison of the primary structures of three pairs of isotypes which differ in their ability to activate complement" J Mol Immunol 16:907-917 ( 1979).

Burton et al., "The Clq Receptor Site on Immunoglobulin G." Nature 288(5789):338-344 (Nov. 27, 1980).

Capel, P., et al., "Heterogeneity of human IgG Fc receptors" Immunomethods 4(1):25-34 (Feb. 1, 1994).

Carter, P., et al., "'Knobs-into-holes' provides a rational design strategy for engineering antibody CH3 domains for heavy chain heterodimerization" Immunotechnology 2(1):73 (Jan. 1996).

Carter, P., et al., "Humanization of an anti-p185 HER2 antibody for human cancer therapy" PNAS USA 89(10):4285-4289 (May 15, 1992).

Charlton, "Expression and Isolation of Recombinant Antibody Fragments in *E. coli*" Methods in Molecular Biology 248:245-254.

Chiang, Austin WT, et al., "Modulating carbohydrate-protein interactions through glycoengineering of monoclonal antibodies to impact cancer physiology" Curr Opin Struc Biol 40:104-111 (Sep. 14, 2016).

Chothia et al., "Canonical structures for the hypervariable regions of immunoglobulins" J Mol Biol 196(4):901-917 (Apr. 23, 1987).

Chromatography "Part A: Fundamentals and Techniques" Heftmann, E. (ed.), 5th edition, New York, NY:Elsevier Science Publishing Company,:(entire book) ( 1992).

Clackson et al., "Making antibody fragments using phage display libraries" Nature 352(6336):624-628 (Aug. 15, 1991).

Dall'Acqua et al., "Antibody humanization by framework shuffling" Methods 36(1):43-60 (Jan. 17, 2005).

de Hass, M., et al., "Fcy receptors of phagocytes" J Lab Clin Med 126(4):330-341 (Oct. 1, 1995).

Deyl, Z., "Advanced Chromatographic and Electromigration Methods in BioSciences" J Chromatogr Lin 60 ( 1998).

Dorokhov, Y.L., et al., "Functional Role of Carbohydrate Residues in Human Immunoglobulin G and Therapeutic Monoclonal Antibodies" Biochemistry-USSR+ 81(8):835-857 (Aug. 1, 2016).

Falkenstein, R., et al., "Targeted Change of the Glycostructure of Therapeutic Monoclonal Antibodies by Combining Affinity" Poster 30th International Symposium on Preparative and Process Chromatography, Philadelphia, PA, pp. 26 ( Jul. 16, 2017).

Fekete, S., et al., "Characterization of cation exchanger stationary phases applied for theseparations of therapeutic monoclonal antibodies" J Pharm Biomed Anal 111:169-176 (Jan. 1, 2015).

Fellouse, F., et al., "Synthetic antibodies from a four-amino-acid code: A dominant role for tyrosine in antigen recognition" PNAS USA 101(34):12467-12472 (Aug. 24, 2004).

Flatman, S., et al., "Process analytics for purification of monoclonal antibodies" J Chromatogr 848(1):79-87 (Mar. 15, 2007).

GE Healthcare LifeSciences-SE et al., "Kappa Select LambdaFabSelect" GE Healthcare LifeSciences-SE: 1-4 (Mar. 12, 2018).

Geisse et al., "Eukaryotic Expression Systems: A Comparison" Protein Expres Purif 8:271-282 ( 1996).

Gerngross, T., "Advances in the Production of Human Therapeutic Proteins in Yeasts and Filamentous Fungi" Nat Biotechnol 22:1409-1414 (Nov. 22, 2004).

Gessner, J., et al., "The IgG Fc Receptor Family" Ann Hematol 76(6):231-248 (Jun. 1, 1998).

Graham, F., et al., "Characteristics of a Human Cell Line Transformed by DNA from Human Adenovirus Type 5" J Gen Virol 36(1):59-74 (Feb. 1, 1977).

Griffiths et al., "Human anti-self antibodies with high specificity from phage display libraries" EMBO J 12(2):725-734 (Feb. 1993).

Gruber et al., "Efficient tumor cell lysis mediated by a bispecific single chain antibody expressed in *Escherichia coli*" J Immunol 152(11):5368-5374 (Mar. 17, 1994).

Hartmann, et al., "Saulenmaterialien in der Biochrornatographie" Abstract Welche Alternativen gibt es zu Protein A Tragern im Capture Schritt?, pp. 1-2 ( Apr. 3, 2014).

Hayes, J., et al., "Glycosylation and Fc Receptors" Curr Top Microbiol 382:165-199 (Jan. 1, 2014).

(56) References Cited

OTHER PUBLICATIONS

Hermanson, et al. Bioconjugate Techniques "Antibody Modification and Conjugation" San Diego:Academic Press, Inc.,: 1-456 (1996).
Hezareh, M., et al., "Effector function activities of a panel of mutants of a broadly neutralizing abtibody against human immunodeficiency virus type 1." J Virol 75(24):12161-12168 (Dec. 1, 2001).
Higel, F., et al., "N-glycosylation heterogeneity and the influence on structure, function and pharmacokinetics of monoclonal antibodies and Fc fusion proteins" Eur J Pharm Biopharm 100(13):94-100 (Jan. 13, 2016).
Hodoniczky, J., et al., "Control of Recombinant Monoclonal Antibody Effector Functions by Fc N-Glycan Remodeling in Vitro" Biotechnol Progr 21(6):1644-1652 (Nov. 30, 2005).
Holliger, P., et al., "Diabodies': Small bivalent and bispecific antibody fragments" PNAS. USA 90(14):6444-6448 (Jul. 15, 1993).
Hoogenboom et al., "By-passing immunisation. Human antibodies from synthetic repertoires of germline V H gene segments rearranged in vitro" J Mol Biol 227(2):381-388 (Sep. 20, 1992).
Hoogenboom et al., "Overview of antibody phage-display technology and its applications" Methods Mol Biol 178:1-37 ( 2002).
Houde, D. et al., "Post-translational Modifications Differentially Affect IgG1 Conformation and Receptor Binding" Mol Cell Proteomics 9(8):1716-1728 (Aug. 1, 2010).
Huang, Wei, et al., "Chemoenzymatic Glycoengineering of Intact IgG Antibodies for Gain of Functions" J Am Chem Soc 134:12308-12318 (Jul. 2, 2012).
Idusogie, E. et al., "Mapping of the C1q Binding Site on Rituxan, A Chimeric Antibody with a Human IgG1 Fc" J Immunol 164(8):4178-4184 (Apr. 15, 2000).
"International Preliminary Report on Patentability—PCT/EP2017/083429":pp. 1-11 (Jul. 4, 2019).
International Preliminary Report on Patentability—PCT/EP2017/083430, dated Jun. 25, 2019, pp. 1-11.
"International Preliminary Report on Patentability—PCT/EP2017/083431":pp. 1-12 (Jul. 4, 2019).
International Search Report—PCT/EP2017/083430 mailed Mar. 14, 2018, dated Mar. 5, 2018, pp. 1-18.
International Search Report—PCT/EP2017/083431 mailed Mar. 6, 2018, dated Feb. 21, 2018, pp. 1-18.
International Search Report—PCT/EP2017/083429 mailed Mar. 23, 2018, dated Mar. 12, 2018, pp. 1-6.
Jefferis, R., et al., "IgG-Fc-mediated effector functions: molecular definition of interaction sites for effector ligands and the role of glycosylation" Immunol Rev 163:59-76 (Jun. 1, 1998).
Jefferis, R., "Glycosylation of recombinant antibody therapeutics" Biotechnol Prog 21(1):11-16 (Jan. 2005).
Kabat et al. et al., "Sequences of Proteins of Immunological Interest" NIH Publication NIH 91-3242 (Fifth Edition), I:647-669 ( 1991).
Kanamori, A., et al., "Deaminated Neuraminic Acid-Rich Glycoprotein of Rainbow Trout Egg Vitelline Envelope" J Biol Chem 265(35):21811-21819 (Dec. 15, 1990).
Kashmiri, S., et al., "SDR grafting-a new approach to antibody humanization" Methods 36:25-34 (Jan. 1, 2005).
Kaufman, "Overview of Vector Design for Mammalian Gene Expression" Mol Biotechnol 16:151-160 ( 2000).
Kindt et al. Kuby Immunol Sixth edition, New York: W. H. Freeman and Company,:91 ( 2007).
Klimka, A., et al., "Human anti-CD30 recombinant antibodies by guided phage antibody selection using cell panning" Br J Cancer 83(2):252-260 (Mar. 1, 2000).
Kostelny, S., et al., "Formation of a bispecific antibody by the use of leucine zippers" J Immunol 148(5):1547-1553 (Mar. 1, 1992).
Kozbor et al., "A Human Hybrid Myeloma for Production of Human Monoclonal Antibodies" J Immunol 133(6):3001-3005 (Dec. 1, 1984).
Kumpel, B., et al., "The biological activity of human monoclonal IgG anti-D is reduced by beta-galactosidase treatment" Hum Antibodies Hybridomas 6(3):82-88 (Jan. 1, 1995).

Kurogochi, M., et al., "Glycoengineered Monoclonal Antibodies with Homogeneous Glycan (M3, G0, G2, and A2) Using a Chemoenzymatic Approach Have Different Affinities for FcγRIIIa and Variable Antibody-Dependent Cellular" PLOS ONE 10:1-24 (Jul. 22, 2015).
Le, Ngoc Phuong, et al., "Immune recruitment or suppression by glycan engineering of endogenous and therapeutic antibodies" Biochim Biophys Acta 1860:1655-1668 (Apr. 20, 2016).
Lee et al., "High-affinity human antibodies from phage-displayed synthetic Fab libraries with a single framework scaffold" J Mol Biol 340(5):1073-1093 (Jul. 23, 2004).
Lee, C., et al., "Bivalent antibody phage display mimics natural immunoglobulin" J Immunol Methods 284(1-2):119-132 (Jul. 30, 2004).
Li, H., et al., "Optimization of humanized IgGs in glycoengineered Pichia pastoris" Nat Biotechnol 24(2):210-215 (Feb. 1, 2006).
Li, J., et al., "Human antibodies for immunotherapy development generated via a human B cell hybridoma technology" PNAS USA 103(10):3557-3562 (Mar. 7, 2006).
Lifely et al., "Glycosylation and Biological Activity of CAMPATH-1H Expressed in Different Cell Lines and Grown Under Different Culture Conditions." Glycobiology 5(8):813-822 (Dec. 1995).
Lin, Chin-Wei, et al., "A common glycan structure on immunoglobulin G for enhancement of effector functions" PNAS 112(34):10611-10616 (Aug. 25, 2015).
Liu et al., "Recovery and purification process development for monoclonal antibody production" mAbs 2(5):480-499 (Sep. 2010).
Lonberg, "Fully human antibodies from transgenic mouse and phage display platforms" Current Opin Immunol 20:450-459 ( 2008).
Lonberg, "Human antibodies from transgenic animals" Nat Biotechnol 23(9):1117-1125 (Sep. 2005).
Love et al., "Recombinant antibodies possessing novel efector functions" Methods Enzymol. 158:515-527 ( 1989).
Lukas et al. et al., "Inhibition of C1-Mediated Immune Hemolysis by Monomeric and Dimeric Peptides from the Second Constant Domain of Human Immunoglobulin G $^1$" J Immunol 127(6):2555-2560 (Dec. 1, 1981).
Luley-Goedl, C., et al., "Two N-terminally truncated variants of human ß-galactoside α2,6 sialyltransferase I with distinct properties for in vitro protein glycosylation" Glycobiology 26(10):1097-1106 (Apr. 21, 2016).
Lund et al., "Oligosaccharide-protein interactions in IgG can modulate recognition by Fcγ receptors" FASEB J 9:115-119 ( 1995).
MacCallum et al., "Antibody-antigen interactions: contact analysis and binding site topography" J Mol Biol 262(5):732-745 (Oct. 11, 1996).
Makrides, S., et al., "Components of Vectors for Gene Transfer and Expression in Mammalian Cells" Protein Expression and Purification 17(2):183-202 (Nov. 1, 1999).
Marks and Bradbury Methods Mol Biol, Antibody Engineering "Selection of human antibodies from phage display libraries" Benny K. C. Lo, Humana Press, vol. 248:161-176 ( 2004).
Marks, J., et al., "By-passing immunization. Human antibodies from V-gene libraries displayed on phage" J Mol Biol 222(3):581-597 (Dec. 5, 1991).
Mather et al., "Culture of testicular cells in hormone-supplemented serum-free medium" Ann NY Acad Sci 383:44-68 ( 1982).
Mather, Jennie, "Establishment and characterization of two distinct mouse testicular epithelial cell lines" Biol Reprod 23(1):243-252 (Aug. 1, 1980).
McCafferty et al., "Phage antibodies: filamentous phage displaying antibody variable domains" Nature 348:552-554 (Dec. 6, 1990).
Milstein et al., "Hybrid hybridomas and their use in immunohistochemistry" Nature 305:537-540 (Oct. 6, 1983).
Mizuochi, T., et al., "Structures of the sugar chains of mouse immunoglobulin G $^1$" Arch Biochem Biophys 257(2):387-394 (Sep. 1, 1987).
Morgan et al., "The N-terminal end of the C$_H$2 domain of chimeric human IgG1 anti-HLA-DR is necessary for C1q, FcγRI and FcγRIII binding" Immunology 86(2):319-324 (Oct. 1995).

(56) References Cited

OTHER PUBLICATIONS

Morrison, S., et al., "Chimeric human antibody molecules: Mouse antigen-binding domains with human constant region domains" PNAS 81(21):6851-6855 (Nov. 1, 1984).
Murphy, C., et al., "Technology advancements in antibody purification" Antibody Tech J 6:17-32 (Aug. 1, 2016).
Nadano, D., et al., "A Naturally Occurring Deaminated Neuraminic Acid3, -I)eoxy- ~-gZycero-~- gaZact-on onulosonic Acid (KDN" J Biol Chem 261(25):11550-11557 (Sep. 5, 1986).
Neuberger et al., "A hapten-specific chimaeric IgE antibody with human physiological effector function" Nature 314:268-270 (Mar. 21, 1985).
Ni, "Research progress and future perspectives in antibodomics and antibodomic drugs" Xiandai Mianyixue ((Abstract only)), 26(4):265-268 ( 2006).
Osbourn, J., et al., "From rodent reagents to human therapeutics using antibody guided selection" Methods 36:61-68 (May 1, 2005).
Padlan, E., "A possible procedure for reducing the immunogenicity of antibody variable domains while preserving their ligand-binding properties" Mol Immunol 28(4-5):489-498 (Apr. 30, 1991).
Parekh et al., "Association of rheumatoid arthritis and primary osteoarthritis with changes in the glycosylation pattern of total serum IgG" Nature 316:452-457 ( 1985).
Poole, Colin, et al. Chromatography Today Fifth edition, Amsterdam, NL:Elsevier Science Publishers, B.V.,:1-1005 ( 1991).
Portolano et al., "Lack of promiscuity in autoantigen-specific H and L chain combinations as revealed by human H and L chanin 'Roulette'" J Immunol 150(3):880-887 (Feb. 1, 1993).
Presta et al., "Humanization of an antibody directed against IgE" J Immunol 151(5):2623-2632 (Sep. 1, 1993).
Presta, Leonard, "Antibody engineering for therapeutics" Curr Opin Struc Biol 13(4):519-525 (Aug. 1, 2003).
Queen, C., et al., "A humanized antibody that binds to the interleukin 2 receptor" PNAS USA 86(24): 10029-10033 (Dec. 1, 1989).
Raju, T., et al., "Terminal sugars of Fc glycans influence antibody effector functions of IgGs" Curr Opin Immunol 20(4):471-478 (Aug. 1, 2008).
Raju, T., "Glycosylation variations with expression systems and their impact on biological activity of therapeutic immunoglobulins" Bioprocess Intl 1:44-53 (Apr. 1, 2003).
Ravetch, J. et al., "IgG Fc receptors" Ann Rev Immunol 19:275-290 ( 2001).
Ravetch, J., et al., "Fc receptors" Annu Rev Immunol 9:457-492 ( 1991).
Reichmann et al., "Reshaping human antibodies for therapy" Nature 332:323-327 (Mar. 24, 1988).
Remington's Pharmaceutical Sciences (Table of Contents, total in 4 pages), Osol et al., 16th edition, Easton, Pennsylvania:Mack Publishing Company, ( 1980).
Roche—Application Note: Malik, Sebastian, et al., entitled "In vitro glycoengineering—Suitability for BioPharma manufacturing", pp. 1-8, Apr. 2016, pp. 1-8.
Rosok et al., "A combinatorial library strategy for the rapid humanization of anticarcinoma BR96 Fab" J Biol Chem 271(37):22611-22618 (Sep. 13, 1996).
Routier, F., et al., "The glycosylation pattern of a humanized IgGI antibody (D1.3) expressed in CHO cells" Glycoconjugate J 14(2):201-207 (Feb. 1, 1997).
Roux, K., et al., "Comparisons of the ability of human IgG3 hinge mutants, IgM, IgE, and IgA2, to form small immune complexes: a role for flexibility and geometry" J Immunol 161(8):4083-4090 (Oct. 15, 1998).
Saba, J., et al., "A study of immunoglobulin G glycosylation in monoclonal and polyclonal species by electrospray and matrix-assisted laser desorption/ionization mass spectrometry" Anal Biochem 305(1):16-31 (Jun. 1, 2002).
Sambrook et al. Molecular Cloning 2nd edition, Cold Spring Harbor Laboratory Press, ( 1989).

Schaefer et al., "Immunoglobulin domain crossover as a generic approach for the production of bispecific IgG antibodies" Proceedings of the National Academy of Sciences 108(27):11187-11192 (Jul. 5, 2011).
Scopes, R. K. Protein Purification: Principles and Practice New York:Springer-Verlag New York Inc., ( 1982).
Shields, R., et al., "High resolution mapping of the binding site on human IgGI for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Sidhu, S., et al., "Phage-displayed antibody libraries of synthetic heavy chain complementarity determining regions" J Mol Biol 338(2):299-310 (Apr. 23, 2004).
Sims, M., et al., "A Humanized CD18 Antibody Can Block Function Without Cell Destruction" J Immunol 151(4):2296-2308 (Aug. 15, 1993).
Taniguchi, T., et al., "Structures of the sugar chains of rabbit immunoglobulin G: Occurrence of asparagine-linked sugar chains in Fab fragment" Biochem 24(20):5551-5557 (Sep. 24, 1985).
Thomann, M., et al., "Fc-galactosylation modulates antibody-dependent cellularcytotoxicity of therapeutic antibodiesMarco" Mol Immunol 73:69-75 (Apr. 6, 2016).
Thomann, M., et al., "In Vitro Glycoengineering of IgG1 and Its Effect on Fc Receptor Binding and ADCC Activity" PLOS ONE 10:1-16 (Jan. 1, 2015).
Thommesen, J., et al., "Lysine 322 in the human IgG3 C(H)2 domain is crucial for antibody dependent complement activation" Mol Immunol 37(16):995-1004 (Nov. 1, 2000).
Traunecker, A., et al., "Bispecific Single Chain Molecules (Janusins) Target Cytotoxic Lymphocytes on HIV Infected Cells" EMBO J 10(12):3655-3659 (Aug. 19, 1991).
Tutt, A., et al., "Trispecific F(ab')$_3$ derivatives that use cooperative signalling via the TCR/CD3 complex and CD2 to activate and redirect resting cytotoxic T cells" J Immunol 147(1):60-69 (Jul. 1, 1991).
Urlaub, G., et al., "Isolation of chinese hamster cell mutants deficient in dihydrofolate reductase activity" PNAS USA 77(7):4216-4220 (Jul. 1980).
van de Winkel et al., "Biology of human immunoglobulin G Fc receptors" J Leukocyte Biol 49(5):511-524 (May 1991).
Van Dijk, M., et al., "Human antibodies as next generation therapeutics" Curr Opin Chem Biol 5(4):368-374 (Aug. 1, 2001).
Varki, A., "Diversity in the sialic acids" Glycobiology 2(1):25-40 (Jan. 1, 1992).
Varki, "Biological Roles of Oligosaccharides: All of the Theories are Correct" Glycobiology 3(2):97-130 (Mar. 31, 1993).
Vijayalakshmi, "Antibody purification methods" Appl Biochem Biotech 75:93-102 (1998).
Vollmers, H., et al., "The 'early birds': Natural IgM antibodies and immune surveillance" Histol Histopathol 20(3):927-937 (Jul. 1, 2005).
Vollmers, H.,, "Death by stress: natural IgM-induced apoptosis" Methods Find Exp Clin Pharmacol 27(3):185-191 (Apr. 1, 2005).
Werner, R., et al., "Appropriate mammalian expression systems for biopharmaceuticals"Arznei-Forschung/Drug Res 48(8):870-880 (Aug. 1, 1998).
Winter et al., "Making antibodies by phage display technology" Annu Rev Immunol 12:433-455 ( 1994).
Wong, S. Chemistry of Protein Conjugation and Cross-Linking Boca Raton, FL USA:CRC Press LLC, (Jan. 1, 1991).
Wright et al., "Effect of glycosylation on antibody function: implications for genetic engineering" Trends Biotechnol. 15(1):26-32 (Jan. 1, 1997).
Yazaki et al., "Expression of recombinant antibodies in mammalian cell lines" Methods Molec Biol 248:255-268 ( 2004).
Ishihara et al., "Optimization of elution salt concentration in stepwise elution of protein chromatography using linear gradient elution data reducing residual protein A by cation-exchange chromatography in monoclonal antibody purification" Journal of Chromatography 1114(1):97-101 ( 2006).
Kisselev, "Polypeptide release factors in prokaryotes and eukaryotes: same function, different structure" Structure 10:8-9 ( 2002).

(56) References Cited

OTHER PUBLICATIONS

Reusch, "Comparison of methods for the analysis of therapeutic immunoglobulin G Fc-glycosylation profiles—part 1: separation-based methods." MAbs 7(1):167-179 ( 2015).
Van Wingerden, "Bio Day Meeting Glycan Introduction Seminar" Denmark, pp. 1-65 ( Mar. 2013).
Whisstock, J.C. et al., "Prediction of protein function from protein sequence and structure" Quarterly Reviews of Biophysics 36(3):307-340 ( 2003).
Witkowski et al., "Conversion of a beta-ketoacyl synthase to a malonyl decarboxylase by replacement of the active-site cysteine with glutamine" Biochemistry 38:11643-11650 ( 1999).
Jones et al., "B-cell-independent sialylation of IgG" PNAS 113(26):7207-7212 ( 2016).
Liu, L., "Antibody Glycosylation and Its Impact on the Pharmacokinetics and Pharmacodynamics of Monoclonal Antibodies and Fc-Fusion Proteins" J Pharm Sci 104(6):1866-1884 (Jun. 1, 2015).
Malik et al., "Implementation of in vitro glycoengineering of monoclonal antibodies into downstream processing of industrial production" Glycobiology 32(2):123-135 (2022).
Qin et al., "Separation and enrichment of O-GlcNAcylated glycoproteins/ glycopeptides" The Chemistry of Life 33(2):59-66 ( 2013).
Raju et al., "Glycoengineering of Therapeutic Glycoproteins: In Vitro Galactosylation and Sialylation of Glycoproteins with Terminal N-Acetylglucosamine and Galactose Residues" Biochemistry 40(30):8868-8876 ( 2001).

\* cited by examiner

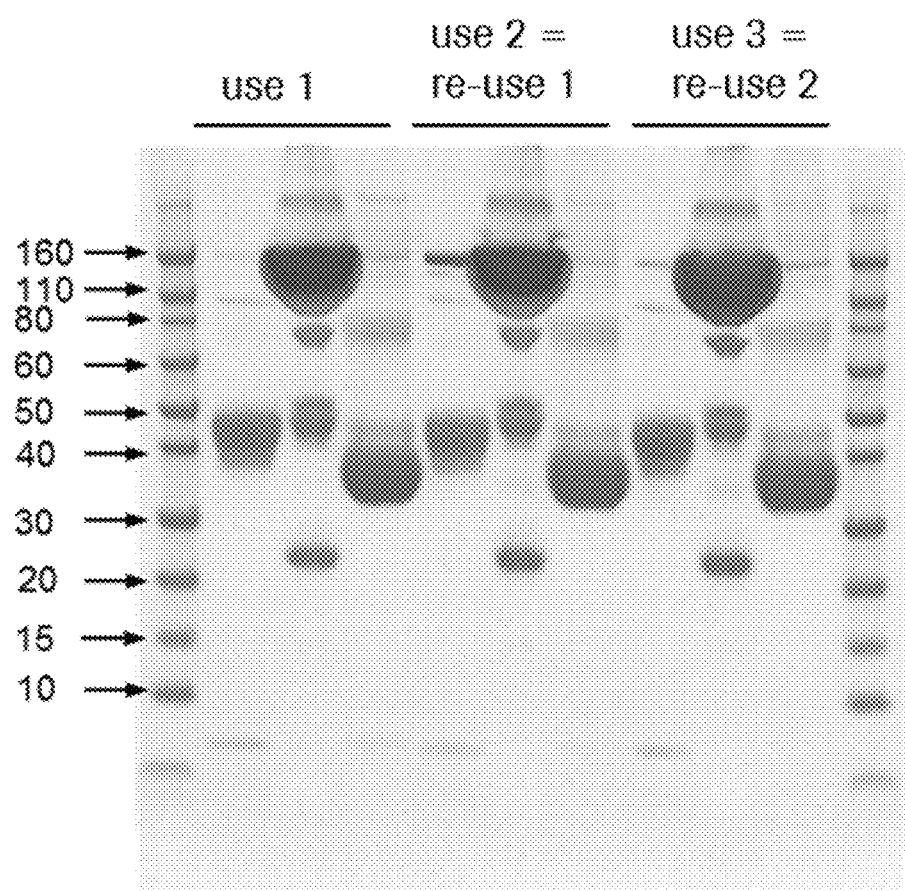

RE-USE OF ENZYMES IN IN VITRO GLYCOENGINEERING OF ANTIBODIES

CROSS-REFERENCE TO RELATED APPLICATION

This application is a continuation of International Patent Application No. PCT/EP2017/083430, having an international filing date of Dec. 19, 2017, the entire contents of which are incorporated herein by reference in its entirety, which claims benefit to European Patent Application No. 16205586.7 filed Dec. 21, 2016 and European Patent Application No. 17157005.4 filed Feb. 20, 2017.

SEQUENCE LISTING

The instant application contains a Sequence Listing submitted via EFS-Web and hereby incorporated by reference in its entirety. Said ASCII copy, created on May 14, 2019, is named P34038-US_Sequence_Listing.txt, and is 60,787 bytes in size.

FIELD OF THE INVENTION

The current invention is in the field of antibody engineering. In more detail herein is reported a method for the in vitro glycoengineering of the glycosylation in the Fc-region of an antibody wherein the used enzymes are recovered and re-used.

BACKGROUND OF THE INVENTION

IgGs are the most abundant antibody isotypes, with IgG1 antibodies being the subclass exhibiting the most significant degree and array of effector functions. IgG1 antibodies are the most commonly used antibodies in immunotherapy, where ADCC and CDC are often deemed important. Within the structure of the antibody, the CH2 domain as well as the IgG hinge region plays a major role in Fc mediated antibody effector functions. Each CH2 domain comprises a conserved glycosylation site at an asparagine residue located at about position 297 (numbering according to EU index of Kabat), at which a glycan moiety is covalently bound (Wright, A. and Morrison, S. L., TIBTECH 15 (1997) 26-32). In the mature IgG molecule, the glycans are buried between the CH2 domains, influencing the tertiary structure of the IgG molecule.

The glycans of the Fc-region of antibodies predominantly are highly heterogeneous complex biantennary structures. While further non-conserved glycosylation sites may be present within the Fab region of an antibody, the influence of antibody glycosylation on its effector functions has been attributed to Fc-region glycosylation.

The N-linked glycans present in the Fc-region of an antibody are known to be essential for the antibody to mediate effector functions such as ADCC (Lively, M. R. et al. Glycobiol. 8 (1995) 813-822; Jefferis R. et al. Immunol Rev. 163 (1998) 59-76). It has been shown that the composition of the N-linked glycan affects the structure of the Fc-region of the IgG molecule and thereby alters antibody effector functions such as Fc-receptor binding, ADCC activity and CDC activity (Presta, L., Curr. Opin. Struct. Biol. 13 (2003) 519-525).

Within IgG antibodies expressed in recombinant expression systems, e.g. by expression in prokaryotic or eukaryotic host cells, the N-linked glycan structure varies between individual antibody molecules. Therefore, antibodies produced in recombinant expression systems can be considered a "population of antibodies" (a term that is further used herein), with antibodies being identical in their amino acid sequence but exhibiting heterogeneity with respect to the N-linked glycan pattern of their Fc-region.

The composition of the Fc-region glycans is known to vary between different host cell species used for expression of recombinant antibodies. Two commonly used host cell lines for the recombinant expression of antibodies are Chinese hamster ovary cells (CHO cells) and mouse myeloma cells (e.g. sp2/0, P3X63Ag8.653, NSO). CHO cells express recombinant antibodies, which are substantially devoid of terminal sialic acid residues, while a major fraction of the glycan patterns are fucosylated. In contrast, mouse myeloma cells give rise to antibody populations with up to 50% (relative frequency) of sialic acid residues but with less of fucose residues.

It is known that some of the terminal residues of the glycan structure influence the IgG effector functions. The presence of a terminal fucose residue is known to contribute to reduced FcgammaRllla binding and to reduced ADCC. Hence, antibodies lacking terminal fucose residues ("afucosylated" antibodies) are associated with an increase of ADCC mediated by the antibody population. While the influence of afucosylation on improvement of ADCC mediation is been widely accepted within the art, the role of Fc-region galactosylation in ADCC mediation is controversially reported. Several studies indicate that galactosylation has no effect on ADCC (Boyd, P. N., et al. Mol Immunol. 32 (1995) 1311-1318; Hodoniczky, J., et al. Biotechnol. Prog. 21 (2005) 1644-1652; Raju, T. S., Curr. Opin. Immunol 20 (2008) 471-478); whereas other studies do report that galactosylation of IgG increases FcgammaRllla binding (Houde, D., et al., Mol. Cell. Proteom. 9 (2010) 1716-1728; Kumpel, B. M., et al., Hum. Antibod. Hybridom. 6 (1995) 82-88; Thomann, M., et al., Mol. Immunol. 73 (2016) 69-75).

Currently, engineering of IgG molecules in order to improve ADCC mediated by the antibodies focuses on adjusting the fucosylation of IgG molecules. Afucosylation of recombinantly expressed IgG may be achieved by expressing antibodies in genetically engineered host cells, e.g. Lec13 CHO cells deficient in protein fucosylation or knockout cell lines, such as CHO cells with a knockout of the alpha-1,6-fucosyltransferase (FUT8) gene.

However, antibodies generated by current expression systems, e.g. CHO cells, exhibit a heterogeneous glycan pattern, leading to variations in the distribution of the distinct glycan species within different batches of generated antibodies. Therefore, there is still a need for tailoring effector functions of recombinant IgG antibodies, especially for the provision of means for improving ADCC mediated by therapeutic antibodies.

In WO 2011/012297 a method for producing an immunoglobulin or immunoglobulin fragment with defined glycostructure comprising the steps of providing an affinity chromatography column eluate containing the immunoglobulin or immunoglobulin fragment, incubating the affinity chromatography column eluate with (a1,3)galactosidase of plant origin, e.g. from green coffee beans (EC 3.2.1.22), applying the incubated affinity chromatography column eluate to a protein A chromatography material and recovering the immunoglobulin or immunoglobulin fragment from the protein A chromatography material and thereby producing an immunoglobulin or immunoglobulin fragment with defined glycostructure is reported.

In WO 2015/123754 an enzymatic method is provided for restructuring an affinity ligand bound heterogeneous glycoform antibody sample to a substantially homogenous single desired glycoform antibody sample for therapeutic uses and kits for performing the methods. A method for enzymatically altering the Fc region of an affinity ligand bound antibody from a heterogeneous glycoform to a substantially homogenous single glycoform comprises: contacting the affinity ligand bound heterogeneous glycoform antibody with a reaction buffer designed for a particular glycoform modification for a time sufficient and under conditions to modify the glycoform of the Fc region to a substantially homogeneous single form; optionally adding one or more nucleotide sugars and/or cofactors; and releasing the substantially homogeneous single glycoform antibody sample from said affinity ligand. The invention also encompasses biopharmaceuticals comprising single glycoform mAbs and polyclonal antibodies enzymatically produced for the treatment of cancers and immune disorders as well as compositions comprising the single glycoform antibodies as a biopharmaceutical.

In WO 2016/037947 galactoengineered recombinant antibodies of IgG1 isotype, methods for the production of said antibodies and uses thereof are reported.

SUMMARY OF THE INVENTION

Herein is reported a method for the in vitro glycoengineering of antibodies, in one embodiment of recombinantly produced monoclonal antibodies, wherein the used enzyme (s) is (are) recovered after the modification of the antibody and conditioned for re-use. The method as reported herein is, amongst other things, an improved method, especially a more economic method, for the modification of antibodies.

With the method as reported herein the enzymes used for the modification of the glycosylation of the antibody can be removed from the antibody preparation resulting in an improved preparation.

The method as reported herein is useful for the modification of any monoclonal antibody without the need of modifications to the preceding up-stream production process steps. The method as reported herein can be integrated into an existing process. Inherently no significant changes to existing antibody producing cell lines are required as the glycostructure modification is provided by the method as reported herein during down-stream processing.

It has been found that it is possible to recover the enzymes use for the modification of the glycosylation of antibodies in a form that allows re-use of the reconditioned enzymes for the same reaction without a detrimental loss of enzymatic activity. It was surprisingly found that the enzymes can be re-used at least once without significant loss of enzymatic activity and conversion efficiency.

One aspect as reported herein is a method for the enzymatic preparation/production of an antibody with a modified (substantially homogeneous) glycosylation at an N-glycosylation site comprising the separation of the enzyme(s) employed in the enzymatic modification from the antibody after the modification of the glycosylation and the re-use of the enzymes at least once (in the same enzymatic preparation/production process).

In one embodiment the separation is by a chromatographic step. In one embodiment the chromatographic step is an affinity chromatography step or/and a cation exchange chromatography step. In one embodiment the affinity chromatography step is a protein A affinity chromatography step or an affinity chromatography with an antibody light chain affinity ligand. In one embodiment the cation exchange chromatography step is a strong cation exchange chromatography step. In one embodiment the strong cation exchange chromatography material has a matrix of cross-linked agarose with sulfopropyl cation exchange groups (SP-Sepharose).

In one embodiment the separation is by two chromatographic steps, wherein the first step is an affinity chromatography step and the second step is a cation exchange chromatography step, wherein the affinity chromatography step is a protein A affinity chromatography step or an affinity chromatography with an antibody light chain affinity ligand, and wherein the cation exchange chromatography step is a cation exchange chromatography step wherein the cation exchange chromatography material has a matrix of cross-linked agarose with sulfopropyl cation exchange groups (SP-Sepharose).

In one embodiment in the enzymatic modification the antibody is either in solution or bound to an antibody (light chain) affinity ligand during the enzymatic modification. In one embodiment the enzymatic modification is in solution.

In one embodiment of the method as reported herein the monoclonal antibody is modified in solution by incubation with one or more glycosylation modifying enzymes to produce a monoclonal antibody preparation with modified glycostructure at an N-glycosylation site, wherein after the incubation the antibody and the one or more enzymes are separated by affinity chromatography or/and cation exchange chromatography, and wherein the enzymes are thereafter re-used at least once in the same reaction.

In one embodiment of the method as reported herein the monoclonal antibody is bound to an affinity ligand, especially an antibody light chain affinity ligand, for enzymatic on-column modification to produce a monoclonal antibody preparation with modified glycostructure at an N-glycosylation site, wherein after the reaction the enzymes are separated from the antibody and re-used at least once in the same reaction.

Thus, in one embodiment the method as reported herein for the enzymatic preparation/production of an antibody with a modified (substantially homogeneous) glycosylation at an N-glycosylation site comprises the following steps
 a) incubating an antibody that has a (non-modified) glycosylation at the N-glycosylation site with one or more enzymes for a time sufficient and under conditions suitable to modify the at the N-glycosylation site to a defined (substantially homogeneous) form (homogeneous glycosylation),
 b) separating the antibody with a modified glycosylation at the N-glycosylation site from the one or more enzymes and thereby producing the antibody with a modified glycosylation at the N-glycosylation site and one or more recycled enzymes, and
 c) repeating step a) with the one or more recycled enzymes of step b) at least once.

In one embodiment in the incubating is either in solution or with the antibody bound to an antibody (light chain) affinity ligand. In one embodiment the incubating is in solution.

It was surprisingly found that an antibody light chain affinity ligand bound antibody can be effectively enzymatically modified as if the antibody would be in solution.

Thus, in one embodiment the method as reported herein for the enzymatic preparation/production of an antibody with a modified (substantially homogeneous) glycosylation at an N-glycosylation site comprises the following steps
 a) incubating in solution an antibody that has a (non-modified) glycosylation at the N-glycosylation site with one or more enzymes for a time sufficient and under conditions suitable to modify the glycosylation at the N-glycosylation site to a defined (substantially homogeneous) form (homogeneous glycosylation), b) separating in one or more chromatography steps the antibody with a modified glycosylation at the N-glycosylation site from the one or more enzymes and thereby producing the antibody with a modified glycosylation at the N-glycosylation site and one or more recycled enzymes, and c) repeating step a) with the one or more recycled enzymes of step b) at least once.

Thus, in one embodiment the method as reported herein for the enzymatic preparation/production of an antibody with a modified (substantially homogeneous) glycosylation at an N-glycosylation site comprises the following steps a) incubating in solution an antibody that has a (non-modified) glycosylation at the N-glycosylation site with one or more enzymes for a time sufficient and under conditions suitable to modify the glycosylation at the N-glycosylation site to a defined (substantially homogeneous) form (homogeneous glycosylation), b) separating the antibody with a modified glycosylation at the N-glycosylation site from the one or more enzymes in a cation exchange chromatography, and thereby producing the antibody with a modified glycosylation at the N-glycosylation site and one or more recycled enzymes, and c) repeating step a) with the one or more recycled enzymes of step b) at least once.

Thus, in one embodiment the method as reported herein for the enzymatic preparation/production of an antibody with a modified (substantially homogeneous) glycosylation at an N-glycosylation site comprises the following steps a) incubating in solution an antibody that has a (non-modified) glycosylation at the N-glycosylation site with one or more enzymes for a time sufficient and under conditions suitable to modify the glycosylation at the N-glycosylation site to a defined (substantially homogeneous) form (homogeneous glycosylation), b) separating the antibody with a modified glycosylation at the N-glycosylation site from the one or more enzymes in an affinity chromatography and thereby producing the antibody with a modified glycosylation at the N-glycosylation site and one or more recycled enzymes, and c) repeating step a) with the one or more recycled enzymes of step b) at least once.

Thus, in one embodiment the method as reported herein for the enzymatic preparation/production of an antibody with a modified (substantially homogeneous) glycosylation at an N-glycosylation site comprises the following steps a) incubating in solution an antibody that has a (non-modified) glycosylation at the N-glycosylation site with two or more enzymes for a time sufficient and under conditions suitable to modify the glycosylation at the N-glycosylation site to a defined (substantially homogeneous) form (homogeneous glycosylation), b) separating the antibody with a modified glycosylation at the N-glycosylation site from the two or more enzymes in an affinity chromatography and thereby producing the antibody with a modified glycosylation at the N-glycosylation site, c) separating the two or more enzymes separated from the antibody in step b) in a cation exchange chromatography, and d) repeating step a) with the two or more separated enzymes of step c) at least once.

In one embodiment the cation exchange chromatography material has a matrix of cross-linked agarose with sulfopropyl cation exchange groups (SP-Sepharose). It has been found that the method is not working with a matrix of crosslinked poly(styrene divinylbenzene).

In one embodiment the one or more enzymes is one enzyme. In one embodiment the one enzyme is a galactosyltransferase or a sialyltransferase.

In one embodiment the two or more enzymes are two enzymes. In one embodiment the two or more enzymes are a galactosyltransferase and a sialyltransferase.

In one embodiment the galactosyltransferase is β4GalT1.

In one embodiment the sialyltransferase is ST6.

In one embodiment the sialyltransferase is ST6Gal1 or ST6Gal2.

In one embodiment of all aspects the N-glycosylation site is in the Fab or in the Fc-region.

In one embodiment the cation exchange chromatography comprises the following steps i) applying the solution comprising a galactosyltransferase and/or a sialyltransferase and the antibody with the modified N-glycosylation site to a (strong) cation exchange chromatography material, ii) optionally washing the (strong) cation exchange chromatography material (to remove unbound compounds from the (strong) cation exchange chromatography material), iii) applying a first solution to the (strong) cation exchange chromatography material and thereby recovering the galactosyltransferase (if present) from the (strong) cation exchange chromatography material, iv) applying a second solution to the (strong) cation exchange chromatography material and thereby recovering the antibody with the modified N-glycosylation site from the (strong) cation exchange chromatography material, and v) applying a linear gradient to the (strong) cation exchange chromatography material and thereby recovering the sialyltransferase (if present) from the (strong) cation exchange chromatography material.

In one embodiment the solution of step i) is a 2-(N-morpholino)ethanesulfonic acid (MES) buffered solution with a pH value from pH 5.0 to pH 6.5. In one embodiment the solution of step i) comprises about 50 mM MES and has a pH value of about pH 6.4.

In one embodiment the solution of step ii) is a 2-(N-morpholino)ethanesulfonic acid (MES) buffered solution with a pH value from pH 5.0 to pH 6.5. In one embodiment the solution of step ii) comprises about 50 mM MES and has a pH value of about pH 6.4.

In one embodiment the solution of step iii) is a tris (hydroxymethyl)aminomethane (TRIS) buffered solution with a pH value from pH 6.6 to pH 8.0. In one embodiment the solution of step iii) comprises about 40 mM TRIS and has a pH value of about pH 7.4.

In one embodiment the solution of step iv) is a 2-(N-morpholino)ethanesulfonic acid (MES) buffered solution with a pH value from pH 5.0 to pH 6.5 comprising about 75 mM to about 125 mM sodium chloride (NaCl). In one embodiment the solution of step iv) comprises about 30 mM MES, about 90 mM NaCl and has a pH value of about pH 5.6.

It has been found that a reduction of the pH value from 7.4 to below pH 6, e.g. pH 5.6, results in the elution of aggregated galactosyltransferase.

In one embodiment the linear gradient is from the solution of step iv) to a 2-(N-morpholino)ethanesulfonic acid (MES)

buffered solution with a pH value from pH 5.0 to pH 6.5 comprising about 750 mM to about 1250 mM sodium chloride (NaCl). In one embodiment the linear gradient is from the solution of step iv) to a solution comprising about 50 mM MES, about 1000 mM NaCl with a pH value of about pH 6.4.

In one embodiment the repeating is for 1, 2, 3, 4, 5, 6, 7, 8, 9 or 10 times. In one embodiment the repeating is for 1 to 5 times. In one embodiment the repeating is for 1 to 3 times.

In one embodiment is the method as reported herein for the enzymatic modification of the glycosylation at an N-glycosylation site of an antibody (to a substantially homogeneous glycosylation) wherein the antibody is bound to an antibody light chain affinity ligand during the enzymatic modification.

In one embodiment of all aspects the method comprises the following steps:
incubating the antibody light chain affinity ligand-bound monoclonal antibody with a glycosylation at the N-glycosylation site with one or more enzymes for a time sufficient and under conditions suitable to modify the glycosylation at the N-glycosylation site to a defined (substantially homogeneous) form (homogeneous glycosylation).

In one embodiment of all aspects the method comprises prior to the incubation step the step of
binding the monoclonal antibody with glycosylation at the N-glycosylation site to an antibody light chain affinity ligand, and after the incubation step the step of
releasing the antibody with a defined (substantially homogeneous) glycosylation at the N-glycosylation site from the antibody light chain affinity ligand.

In one embodiment of all aspects the method comprises the following steps in the following order
applying a (buffered) solution comprising the antibody with glycosylation at the N-glycosylation site to an antibody light chain affinity ligand bound to a solid phase (antibody light chain affinity ligand chromatography material) whereby the antibody is bound to the ligand (resulting in a ligand-bound antibody),
optionally washing the solid phase with a buffered solution,
enzymatically modifying the glycosylation at the N-glycosylation site of the antibody by either
applying a first (buffered) solution comprising a first glycosylation modifying enzyme (and a first activated sugar residue) for a time sufficient and under conditions suitable for the enzymatic modification to the ligand-bound antibody, optionally washing the modified ligand-bound antibody, applying a second (buffered) solution comprising a second glycosylation modifying enzyme (and a second activated sugar) for a time sufficient and under conditions suitable for the enzymatic modification to the modified ligand-bound antibody, optionally washing the two-times modified ligand-bound antibody,
or
applying a first (buffered) solution comprising a first glycosylation modifying enzyme (and a first activated sugar) for a time sufficient and under conditions suitable for at least a partial enzymatic modification to the ligand-bound antibody, applying after a defined period of time a second (buffered) solution comprising a second glycosylation modifying enzyme (and a second activated sugar) for a time sufficient and under conditions suitable for the enzymatic modification to the modified ligand-bound antibody, optionally washing the two-times modified ligand-bound antibody,
or
applying a (buffered) solution comprising a first and a second glycosylation modifying enzyme (and a first and second activated sugar) for a time sufficient and under conditions suitable for the enzymatic modification of the ligand-bound antibody, optionally washing the modified ligand-bound antibody,
releasing the antibody with a defined glycosylation at the N-glycosylation site from the antibody light chain affinity ligand.

The antibodies as used in the methods as reported herein can be any antibody or antibody fragment, including Fab fragments, single chain antibodies, multispecific antibodies and antibody fusions.

Thus, in one embodiment of all aspects as reported herein the antibody is selected from the group of antibodies consisting of an antibody Fab fragment, a full length antibody, a bivalent monospecific antibody, a bispecific antibody, a bivalent bispecific antibody, a trivalent bispecific antibody, a tetravalent bispecific antibody, a trivalent trispecific antibody, and a tetravalent tetraspecific antibody.

In one embodiment the antibody is a bivalent monospecific antibody.

In one embodiment the antibody is a bivalent or trivalent or tetravalent bispecific antibody.

In one embodiment the antibody is a chimeric or humanized or human antibody.

In one embodiment the antibody is a polyclonal antibody preparation.

In one embodiment the antibody is a monoclonal antibody.

In one embodiment of all aspects as reported herein the antibody (preparation) is an antibody (preparation) of the human IgG class. In one embodiment the antibody is an antibody of the human IgG1 or IgG4 subclass.

In one embodiment of all aspects as reported herein the defined glycosylation is a glycosylation selected from the group consisting of G2 glycoform, G0 glycoform, M3 glycoform, S2 glycoform, A2B glycoform, A2BG2 glycoform and S1 glycoform.

In one embodiment of all aspects as reported herein the defined glycosylation is a glycosylation selected from the group consisting of galactose as the terminal sugar, GlcNAc as the terminal sugar, mannose as the terminal sugar and sialic acid as the terminal sugar.

In one embodiment the antibody is a recombinantly produced antibody.

One aspect as reported herein is an antibody produced with a method as reported herein.

One aspect as reported herein is a pharmaceutical formulation comprising an antibody with defined glycosylation produced by a method as reported herein.

Another aspect of the invention is a method for the recombinant production of an antibody or fragment thereof with defined glycosylation at an N-glycosylation site, comprising the steps of
a) recombinantly producing an antibody (of IgG1 isotype) or a fragment thereof in a (mammalian or CHO) cell, which comprises nucleic acids encoding the antibody or fragment thereof, to obtain an antibody or fragment thereof with glycosylation at the N-glycosylation site,
b) isolating (recovering and optionally purifying) the antibody or fragment thereof with heterogeneous glycosylation at the N-glycosylation site, c) enzymatically modifying the antibody or fragment thereof with glycosylation at the N-glycosylation site with galactosyltransferase and/or a sialyl transferase to obtain an antibody or fragment thereof with defined at the N-glycosylation site, which comprises a relative amount of at least 70% bi-galactosylated antibodies (G2F glycoform) (wherein 100% corresponds to the amount of G0F, G1F and G2F glycoforms) at the N-glycosylation site, and subsequent separation of the of the modified antibody from the enzyme(s) with a method as reported herein, d) optionally purifying the modified antibody or fragment thereof by one or more chromatography steps, and thereby producing an antibody or fragment thereof with defined glycosylation at the N-glycosylation site.

In one embodiment of all aspects as reported herein the first glycosylation modifying enzyme is a galactosyltransferase.

In one embodiment of all aspects as reported herein the first glycosylation modifying enzyme is a galactosyltransferase and the second glycosylation modifying enzyme is a sialyltransferase.

In one embodiment the galactosyltransferase is β4GalT1.

In one embodiment the sialyltransferase is ST6.

In one embodiment the sialyltransferase is ST6Gal1 or ST6Gal2.

In one embodiment the (first) buffered solution comprises UDP-Gal.

In one embodiment the (second) buffered solution comprises CMP-NANA.

In one embodiment the incubation is at room temperature (20-25° C., preferably about 22° C.).

In one embodiment the incubation is at 25° C.

In one embodiment the incubation is at 37° C.

In one embodiment the incubation is for 7 to 48 hours.

In one embodiment of all aspects as reported herein the solution comprises a chromatographically purified antibody, the (first) glycosylation modifying enzyme is GalT1, and the incubation with the (first) glycosylation modifying enzyme is for 24 hours at 20-27° C. or 37° C. In one embodiment the incubation is at room temperature (about 22° C.).

In one embodiment of all aspects as reported herein the solution comprises a chromatographically purified antibody, the (second) glycosylation modifying enzyme is ST6, and the incubation with the (second) glycosylation modifying enzyme is for 24 hours at 20-27° C. or 37° C. In one embodiment the incubation is at room temperature (about 22° C.).

In one embodiment of all aspects as reported herein the solution is a buffered, cell-free cultivation supernatant comprising the antibody, the first glycosylation modifying enzyme is GalT1, the second glycosylation modifying enzyme is ST6, which is added 6 to 24 hours, preferably 24 hours, after the first glycosylation modifying enzyme, the total incubation time is 24 hours to 48 hours, preferably 30 hours, at 20-27° C. or 37° C. In one embodiment the incubation is at room temperature (about 22° C.).

One aspect as reported herein is a method for producing an antibody comprising the following steps in the following order:

providing a cell comprising a nucleic acid encoding the antibody or a fragment thereof comprising at least an antibody light chain, cultivating the cell under conditions suitable for the expression of the antibody or fragment thereof with glycosylation at an N-glycosylation site (the fragment comprises at least on light chain that can specifically be bound by the antibody light chain affinity chromatography material used in one of the next steps), recovering the antibody or fragment thereof from the cell or the cultivation medium, optionally applying a solution comprising antibody or fragment thereof to an antibody light chain affinity chromatography column under conditions suitable for binding of the antibody or fragment thereof to the affinity chromatography material, modifying the glycosylation of the antibody or fragment thereof at the N-glycosylation site with a method as reported herein, and recovering the modified antibody or fragment thereof with a defined glycosylation at the N-glycosylation site, and thereby producing an antibody.

In one embodiment comprises the method the following step as final step:

purifying the modified antibody or fragment thereof with one to three chromatography steps.

One aspect as reported herein is a chromatographic method for the separation of a mixture comprising a galactosyltransferase or/and a sialyltransferase and an antibody using a cation exchange chromatography material comprising the following steps i) applying the solution comprising the galactosyltransferase and/or the sialyltransferase and the antibody to a (strong) cation exchange chromatography material, ii) optionally washing the (strong) cation exchange chromatography material (to remove unbound compounds from the (strong) cation exchange chromatography material), iii) applying a first solution to the (strong) cation exchange chromatography material and thereby recovering the galactosyltransferase (if present) from the (strong) cation exchange chromatography material, iv) applying a second solution to the (strong) cation exchange chromatography material and thereby recovering the antibody from the (strong) cation exchange chromatography material, and v) applying a linear gradient to the (strong) cation exchange chromatography material and thereby recovering the sialyltransferase (if present) from the (strong) cation exchange chromatography material.

It has been found that with this method the separated galactosyltransferase as well as the separated sialyltransferase can be re-used in an enzymatic conversion without significant loss of enzymatic activity or/and selectivity for multiple times, i.e. at least three times.

In one embodiment the solution of step i) is a 2-(N-morpholino)ethanesulfonic acid (MES) buffered solution with a pH value from pH 5.0 to pH 6.5. In one embodiment the solution of step i) comprises about 50 mM MES and has a pH value of about pH 6.4.

In one embodiment the solution of step ii) is a 2-(N-morpholino)ethanesulfonic acid (MES) buffered solution with a pH value from pH 5.0 to pH 6.5. In one embodiment the solution of step ii) comprises about 50 mM MES and has a pH value of about pH 6.4.

In one embodiment the solution of step iii) is a tris (hydroxymethyl)aminomethane (TRIS) buffered solution with a pH value from pH 6.6 to pH 8.0. In one embodiment the solution of step iii) comprises about 40 mM TRIS and has a pH value of about pH 7.4.

In one embodiment the solution of step iv) is a 2-(N-morpholino)ethanesulfonic acid (MES) buffered solution with a pH value from pH 5.0 to pH 6.5 comprising about 75 mM to about 125 mM sodium chloride (NaCl). In one embodiment the solution of step iv) comprises about 30 mM MES, about 90 mM NaCl and has a pH value of about pH 5.6.

It has been found that a reduction of the pH value from 7.4 to 5.6 results in the elution of aggregated galactosyltransferase.

In one embodiment the linear gradient is from the solution of step iv) to a 2-(N-morpholino)ethanesulfonic acid (MES) buffered solution with a pH value from pH 5.0 to pH 6.5 comprising about 750 mM to about 1250 mM sodium chloride (NaCl). In one embodiment the linear gradient is from the solution of step iv) to a solution comprising about 50 mM MES, about 1000 mM NaCl with a pH value of about pH 6.4.

In one embodiment of all aspects the N-glycosylation site is in the Fab or in the Fc-region.

DETAILED DESCRIPTION OF THE INVENTION

Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype. Specifically the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody-dependent cellular cytotoxicity (ADCC)" is a function mediated by Fc receptor binding and refers to lysis of target cells by an antibody as reported herein in the presence of effector cells. ADCC is measured in one embodiment by the treatment of a preparation of CD19 expressing erythroid cells (e.g. K562 cells expressing recombinant human CD19) with an antibody as reported herein in the presence of effector cells such as freshly isolated PBMC (peripheral blood mononuclear cells) or purified effector cells from buffy coats, like monocytes or NK (natural killer) cells. Target cells are labeled with Cr-51 and subsequently incubated with the antibody. The labeled cells are incubated with effector cells and the supernatant is analyzed for released Cr-51. Controls include the incubation of the target endothelial cells with effector cells but without the antibody. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In one preferred embodiment binding to FcγR on NK cells is measured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "complement-dependent cytotoxicity (CDC)" refers to lysis of cells induced by the antibody as reported herein in the presence of complement. CDC is measured in one embodiment by the treatment of CD19 expressing human endothelial cells with an antibody as reported herein in the presence of complement. The cells are in one embodiment labeled with calcein. CDC is found if the antibody induces lysis of 20% or more of the target cells at a concentration of 30 µg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate]).

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol 19 (2001) 275-290). Such receptors are FcγRI, FcγRIIA and FcγRIIIA. The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119; Morgan, A., et al, Immunology 86 (1995) 319-324; and EP 0 307 434).

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, or from Ala 231 to the carboxyl-terminus of the heavy chain. However, the C-terminal lysine (Lys447) of the Fc-region may or may not be present.

The antibodies as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E and/or P329G (numbering according to EU index of Kabat). In one embodiment the Fc-region is of the human IgG1 subclass comprising the mutations L234A and L235A and optionally P329G (numbering according to EU index of Kabat).

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof. Wild-type Fc-regions are denoted in SEQ ID NO: 01 (IgG1, caucasian allotype), SEQ ID NO: 02 (IgG1, afroamerican allotype), SEQ ID NO: 03 (IgG2), SEQ ID NO: 04 (IgG3) and SEQ ID NO: 05 (IgG4).

Variant (human) Fc-regions are defined by the amino acid mutations that are contained. Thus, for example, the term P329G denotes a variant Fc-region with the mutation of proline to glycine at amino acid position 329 relative to the parent (wild-type) Fc-region (numbering according to EU index of Kabat). The identity of the wild-type amino acid may be unspecified, in which case the aforementioned variant is referred to as 329G.

A polypeptide chain of a wild-type human Fc-region of the IgG1 subclass has the following amino acid sequence starting with a cysteine residue at position 227 and ending with a glycine residue at position 446:

```
                                            (SEQ ID NO: 06)
CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR (E/D)E(M/L)TKNQVSL TCLVKGFYPS

DIAVEWESNG QPENNYKTTP PVLDSDGSFF LYSKLTVDKS

RWQQGNVFSC SVMHEALHNH YTQKSLSLSP G.
```

A polypeptide chain of a variant human Fc-region of the IgG1 subclass with the mutations T366S, L368A and Y407V has the following amino acid sequence:

```
                                            (SEQ ID NO: 07)
CPPCPAPELL GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR DELTKNQVSL SCAVKGFYPS DIAVEWESNG

QPENNYKTTP PVLDSDGSFF LVSKLTVDKS RWQQGNVFSC

SVMHEALHNH YTQKSLSLSP G.
```

A polypeptide chain of a variant human Fc-region of the IgG1 subclass with the mutation T366W has the following amino acid sequence:

```
                                            (SEQ ID NO: 08)
CPPCPAPELL GGPSVFLFPP PKKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR DELTKNQVSL WCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A and L235A has the following amino acid sequence:

```
                                            (SEQ ID NO: 09)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR DELTKNQVSL TCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A, L235A, T366S, L368A and Y407V has the following amino acid sequence:

```
                                            (SEQ ID NO: 10)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR DELTKNQVSL SCAVKGFYPS DIAVEWESNG

QPENNYKTTP PVLDSDGSFF LVSKLTVDKS RWQQGNVFSC

SVMHEALHNH YTQKSLSLSP G.
```

A polypeptide chain of a variant human Fc-region of the IgG1 subclass with the mutations L234A, L235A and T366W has the following amino acid sequence:

```
                                            (SEQ ID NO: 11)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE

PQVYTLPPSR DELTKNQVSL WCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A, L235A and P329G has the following amino acid sequence:

```
                                            (SEQ ID NO: 12)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVYTLPPSR DELTKNQVSL TCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A, L235A, P329G, T366S, L368A and Y407V has the following amino acid sequence:

```
                                            (SEQ ID NO: 13)
CPPCPAPEAA GGPSVFLFPP KPKDTLMISR TPEVTCVVVD

VSHEDPEVKF NWYVDGVEVH NAKTKPREEQ YNSTYRVVSV
```

```
LTVLHQDWLN GKEYKCKVSN KALGAPIEKT ISKAKGQPRE

PQVYTLPPSR DELTKNQVSL SCAVKGFYPS DIAVEWESNG

QPENNYKTTP PVLDSDGSFF LVSKLTVDKS RWQQGNVFSC

SVMHEALHNH YTQKSLSLSP G.
```

A polypeptide chain of a variant human Fc-region of the IgG1 subclass with the mutations L234A, L235A, P329G and T366W has the following amino acid sequence:

```
                                        (SEQ ID NO: 14)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVYTLPPSR DELTKNQVSL WCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A, L235A, P329G, Y349C, T366S, L368A and Y407V has the following amino acid sequence:

```
                                        (SEQ ID NO: 15)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVCTLPPSR DELTKNQVSL SCAVKGFYPS DIAVEWESNG

QPENNYKTTP PVLDSDGSFF LVSKLTVDKS RWQQGNVFSC

SVMHEALHNH YTQKSLSLSP G.
```

A polypeptide chain of a variant human Fc-region of the IgG1 subclass with the mutations L234A, L235A, P329G, S354C and T366W has the following amino acid sequence:

```
                                        (SEQ ID NO: 16)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVYTLPPCR DELTKNQVSL WCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations L234A, L235A, P329G, S354C, T366S, L368A and Y407V has the following amino acid sequence:

```
                                        (SEQ ID NO: 17)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVYTLPPCR DELTKNQVSL SCAVKGFYPS DIAVEWESNG

QPENNYKTTP PVLDSDGSFF LVSKLTVDKS RWQQGNVFSC

SVMHEALHNH YTQKSLSLSP G.
```

A polypeptide chain of a variant human Fc-region of the IgG1 subclass with the mutations L234A, L235A, P329G, Y349C and T366W has the following amino acid sequence:

```
                                        (SEQ ID NO: 18)
CPPCPAPEAA GGPSVFLFPP KPKDTLMISR TPEVTCVVVD

VSHEDPEVKF NWYVDGVEVH NAKTKPREEQ YNSTYRVVSV

LTVLHQDWLN GKEYKCKVSN KALGAPIEKT ISKAKGQPRE

PQVCTLPPSR DELTKNQVSL WCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a variant human Fc-region of the IgG1 subclass with the mutations I253A, H310A and H435A has the following amino acid sequence:

```
                                        (SEQ ID NO: 19)
CPPCPAPELL GGPSVFLFPP KPKDTLMASR TPEVTCVVVD

VSHEDPEVKF NWYVDGVEVH NAKTKPREEQ YNSTYRVVSV

LTVLAQDWLN GKEYKCKVSN KALPAPIEKT ISKAKGQPRE

PQVYTLPPSR DELTKNQVSL TCLVKGFYPS DIAVEWESNG

QPENNYKTTP PVLDSDGSFF LYSKLTVDKS RWQQGNVFSC

SVMHEALHNA YTQKSLSLSP G.
```

A polypeptide chain of a variant human Fc-region of the IgG1 subclass with the mutations H310A, H433A and Y436A has the following amino acid sequence:

```
                                        (SEQ ID NO: 20)
CPPCPAPELL GGPSVFLFPP KPKDTLMISR TPEVTCVVVD

VSHEDPEVKF NWYVDGVEVH NAKTKPREEQ YNSTYRVVSV

LTVLAQDWLN GKEYKCKVSN KALPAPIEKT ISKAKGQPRE

PQVYTLPPSR DELTKNQVSL TCLVKGFYPS DIAVEWESNG

QPENNYKTTP PVLDSDGSFF LYSKLTVDKS RWQQGNVFSC

SVMHEALANH ATQKSLSLSP G.
```

A polypeptide chain of a variant human Fc-region of the IgG1 subclass with the mutations M252Y, S254T and T256E has the following amino acid sequence:

```
                                        (SEQ ID NO: 21)
CPPCPAPELL GGPSVFLFPP KPKDTLYITR EPEVTCVVVD

VSHEDPEVKF NWYVDGVEVH NAKTKPREEQ YNSTYRVVSV

LTVLHQDWLN GKEYKCKVSN KALPAPIEKT ISKAKGQPRE
```

```
                                            (SEQ ID NO: 21 continued)
PQVYTLPPSR DELTKNQVSL TCLVKGFYPS DIAVEWESNG

QPENNYKTTP PVLDSDGSFF LYSKLTVDKS RWQQGNVFSC

SVMHEALHNH YTQKSLSLSP G.
```

A polypeptide chain of a wild-type human Fc-region of the IgG4 subclass has the following amino acid sequence:

```
                                            (SEQ ID NO: 22)
CPSCPAPEFL GGPSVFLFPP KPKDTLMISR TPEVTCVVVD

VSQEDPEVQF NWYVDGVEVH NAKTKPREEQ FNSTYRVVSV

LTVLHQDWLN GKEYKCKVSN KGLPSSIEKT ISKAKGQPRE

PQVYTLPPSQ EEMTKNQVSL TCLVKGFYPS DIAVEWESNG

QPENNYKTTP PVLDSDGSFF LYSRLTVDKS RWQEGNVFSC

SVMHEALHNH YTQKSLSLSL G.
```

A polypeptide chain of a variant human Fc-region of the IgG4 subclass with the mutations S228P and L235E has the following amino acid sequence:

```
                                            (SEQ ID NO: 23)
CPPCPAPEFE GGPSVFLFPP KPKDTLMISR TPEVTCVVVD

VSQEDPEVQF NWYVDGVEVH NAKTKPREEQ FNSTYRVVSV

LTVLHQDWLN GKEYKCKVSN KGLPSSIEKT ISKAKGQPRE

PQVYTLPPSQ EEMTKNQVSL TCLVKGFYPS DIAVEWESNG

QPENNYKTTP PVLDSDGSFF LYSRLTVDKS RWQEGNVFSC

SVMHEALHNH YTQKSLSLSL G.
```

A polypeptide chain of a variant human Fc-region of the IgG4 subclass with the mutations S228P, L235E and P329G has the following amino acid sequence:

```
                                            (SEQ ID NO: 24)
CPPCPAPEFE GGPSVFLFPP KPKDTLMISR TPEVTCVVVD

VSQEDPEVQF NWYVDGVEVH NAKTKPREEQ FNSTYRVVSV

LTVLHQDWLN GKEYKCKVSN KGLGSSIEKT ISKAKGQPRE

PQVYTLPPSQ EEMTKNQVSL TCLVKGFYPS DIAVEWESNG

QPENNYKTTP PVLDSDGSFF LYSRLTVDKS RWQEGNVFSC

SVMHEALHNH YTQKSLSLSL G.
```

A polypeptide chain of a variant human Fc-region of the IgG4 subclass with the mutations S228P, L235E, P329G, T366S, L368A and Y407V has the following amino acid sequence:

```
                                            (SEQ ID NO: 25)
ESKYGPPCPP CPAPEFEGGP SVFLFPPKPK DTLMISRTPE

VTCVVVDVSQ EDPEVQFNWY VDGVEVHNAK TKPREEQFNS

TYRVVSVLTV LHQDWLNGKE YKCKVSNKGL GSSIEKTISK

AKGQPREPQV YTLPPSQEEM TKNQVSLSCA VKGFYPSDIA

VEWESNGQPE NNYKTTPPVL DSDGSFFLVS RLTVDKSRWQ

EGNVFSCSVM HEALHNHYTQ KSLSLSLG.
```

A polypeptide chain of a variant human Fc-region of the IgG4 subclass with the mutations S228P, L235E, P329G and T366W has the following amino acid sequence:

```
                                            (SEQ ID NO: 26)
ESKYGPPCPP CPAPEFEGGP SVFLFPPKPK DTLMISRTPE

VTCVVVDVSQ EDPEVQFNWY VDGVEVHNAK TKPREEQFNS

TYRVVSVLTV LHQDWLNGKE YKCKVSNKGL GSSIEKTISK

AKGQPREPQV YTLPPSQEEM TKNQVSLWCL VKGFYPSDIA

VEWESNGQPE NNYKTTPPVL DSDGSFFLYS RLTVDKSRWQ

EGNVFSCSVM HEALHNHYTQ KSLSLSLG.
```

The terms "full length antibody", "intact antibody," and "whole antibody" are used herein interchangeably to refer to an antibody having a structure substantially similar to a native antibody structure or having heavy chains that contain an Fc-region as defined herein.

The term "glycan" denotes a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of β-glycosidic linkages between monosaccharides. Glycans can be homo- or heteropolymers of monosaccharide residues, and can be linear or branched.

The term "glycosyltransferase" denotes an enzyme capable of transferring the monosaccharide moiety from a nucleotide sugar to an acceptor molecule such as a sugar molecule in an oligosaccharide. Examples of such glycosyltransferase include, but not limited to galactosyltransferase and sialyltransferase.

The term "hinge region" denotes the part of an antibody heavy chain polypeptide that joins in a wild-type antibody heavy chain the CH1 domain and the CH2 domain, e.g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. The hinge region generally comprises about 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083).

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "isolated" antibody is one, which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "light chain" denotes the shorter polypeptide chains of native IgG antibodies. The light chain of an antibody may be assigned to one of two types, called kappa (κ) and lambda (λ), based on the amino acid sequence of its constant domain, see SEQ ID NO: 27 for a human kappa light chain constant domain and SEQ ID NO: 28 for a human lambda light chain constant domain.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "N-linked oligosaccharide" denotes oligosaccharides that are linked to the peptide backbone at an asparagine amino acid residue, by way of an asparagine-N-acetyl glucosamine linkage. N-linked oligosaccharides are also called "N-glycans." All N-linked oligo saccharides have a common pentasaccharide core of Man3GlcNAc2. They differ in the presence of, and in the number of branches (also called antennae) of peripheral sugars such as N-acetyl glucosamine, galactose, N-acetyl galactosamine, fucose and sialic acid. Optionally, this structure may also contain a core fucose molecule and/or a xylose molecule.

The term "O-linked oligosaccharide" denotes oligosaccharides that are linked to the peptide backbone at a threonine or serine amino acid residue.

The term "sialic acid" denotes any member of a family of nine-carbon carboxylated sugars. The most common member of the sialic acid family is N-acetyl-neuraminic acid (2-keto-5-acetamido-3,5-dideoxy-D-glycero-D-galac-tononulopyranos-1-onic acid (often abbreviated as Neu5Ac, NeuAc, or NANA). A second member of the family is N-glycolyl neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O—C1-C6 acyl-NeuSAc like 9-O-lactyl-Neu5Ac or 9-O-acetyl-NeuSAc, 9-deoxy-9-fluoro-Neu5Ac and 9-azido-9-deoxyNeu5Ac. For review of the sialic acid family, see, e.g., Varki, Glycobiol. 2 (1992) 25-40; Sialic Acids: Chemistry, Metabolism and Function, R. Schauer, Ed. (Springer-Verlag, New York (1992)). The synthesis and use of sialic acid compounds in a sialylation procedure is reported in WO 92/16640, the disclosure of which is incorporated herein in its entirety.

With respect to antibodies, the term "substantially" denotes that the respective product (antibody) has a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, 96%, 97%, 98% and most preferably at least about 99%, by weight, of the desired antibody.

The term "glycosylation state" denotes a specific or desired glycosylation pattern of an antibody. A "glycoform" is an antibody comprising a particular glycosylation state. Such glycosylation patterns include, for example, attaching one or more sugars at position N-297 of the Fc-region of an antibody (numbering according to Kabat), wherein said sugars are produced naturally, recombinantly, synthetically, or semi-synthetically. The glycosylation pattern can be determined by many methods known in the art. For example, methods of analyzing carbohydrates on proteins have been reported in US 2006/0057638 and US 2006/0127950 (the disclosures of which are hereby incorporated by reference in their entirety).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W. H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "N-glycosylation site" denotes the amino acid residue within an N-glycosylation site consensus sequence to which a glycan is or can be attached. Generally N-linked glycans are attached to the amid nitrogen atom of an asparagine amino acid (Asn, N) side chain. The N-glycosylation site consensus sequence is Asn-X-Ser/Thr, wherein X can be any amino acid residue except proline. The term "N-linked glycosylation" denotes the result of the attachment of a sugar molecule oligosaccharide (denotes as glycan) to e.g. the amide nitrogen atom of asparagine.

Antibody Glycosylation

Human antibodies are mainly glycosylated at the asparagine residue at about position 297 (Asn297) of the heavy chain CH2 domain or in the Fab region with a more or less fucosylated biantennary complex oligosaccharide (antibody amino acid residue numbering according to Kabat, supra). The biantennary glycostructure can be terminated by up to two consecutive galactose (Gal) residues in each arm. The arms are denoted (1,6) and (1,3) according to the glycoside bond to the central mannose residue. The glycostructure denoted as G0 comprises no galactose residue. The glycostructure denoted as G1 contains one or more galactose residues in one arm. The glycostructure denoted as G2 contains one or more galactose residues in each arm (Raju, T. S., Bioprocess Int. 1 (2003) 44-53). Human constant heavy chain regions are reported in detail by Kabat, supra, and by Brueggemann, M., et al., J. Exp. Med. 166 (1987) 1351-1361; Love, T. W., et al., Methods Enzymol. 178 (1989) 515-527. CHO type glycosylation of antibody Fc-regions is e.g. described by Routier, F. H., Glycoconjugate J. 14 (1997) 201-207.

The term "antibody" denotes and encompasses the various forms of antibodies such as human antibodies, humanized antibodies, chimeric antibodies, or T-cell antigen depleted antibodies (see e.g. WO 98/33523, WO 98/52976, and WO 00/34317). In one embodiment the antibody in the methods as reported herein is a human or humanized antibody. Genetic engineering of antibodies is e.g. described in Morrison, S. L., et al., Proc. Natl. Acad. Sci. USA 81 (1984) 6851-6855; U.S. Pat. Nos. 5,202,238 and 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

An antibody in general comprises two so called full length light chain polypeptides (light chain) and two so called full length heavy chain polypeptides (heavy chain). Each of the full length heavy and light chain polypeptides contains a variable domain (variable region) (generally the amino terminal portion of the full length polypeptide chain) comprising binding regions, which interact with an antigen. Each of the full length heavy and light chain polypeptides comprises a constant region (generally the carboxyl terminal portion). The constant region of the full length heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of a full length antibody's light or heavy chain in turn comprises different segments, i.e. four framework regions (FR) and three hypervariable regions (CDR). A "full length antibody heavy chain" is a polypeptide consisting in N-terminal to C-terminal direction of an antibody heavy chain variable domain (VH), an antibody constant domain 1 (CH1), an antibody hinge region, an antibody constant domain 2 (CH2), an antibody constant domain 3 (CH3), and optionally an antibody constant domain 4 (CH4) in case of an antibody of the subclass IgE. A "full length antibody light chain" is a polypeptide consisting in N-terminal to C-terminal direction of an antibody light chain variable domain (VL), and an antibody light chain constant domain (CL). The full length antibody chains a linked together via inter-polypeptide disulfide bonds between the CL-domain and the CH1 domain and between the hinge regions of the full length antibody heavy chains.

It has been reported in recent years that the glycosylation pattern of antibodies, i.e. the saccharide composition and multitude of attached glycostructures, has a strong influence on the biological properties (see e.g. Jefferis, R., Biotechnol. Prog. 21 (2005) 11-16). Antibodies produced by mammalian cells contain 2-3% by mass oligosaccharides (Taniguchi, T., et al., Biochem. 24 (1985) 5551-5557). This is equivalent e.g. in an antibody of class G (IgG) to 2.3 oligosaccharide residues in an IgG of mouse origin (Mizuochi, T., et al., Arch. Biochem. Biophys. 257 (1987) 387-394) and to 2.8 oligosaccharide residues in an IgG of human origin (Parekh, R. B., et al., Nature 316 (1985) 452-457), whereof generally two are located in the Fc-region at Asn297 and the remaining in the variable region (Saba, J. A., et al., Anal. Biochem. 305 (2002) 16-31).

The term "glycostructure" as used within this application denotes a single, defined N- or O-linked oligosaccharide at a specified amino acid residue. Thus, the term "antibody with a G1 glycostructure" denotes an antibody comprising at the asparagine amino acid residue at about amino acid position 297 according to the Kabat numbering scheme or in the FAB region a biantennary oligosaccharide comprising only one terminal galactose residue at the non-reducing ends of the oligosaccharide. The term "oligosaccharide" as used within this application denotes a polymeric saccharide comprising two or more covalently linked monosaccharide units.

For the notation of the different N- or O-linked oligosaccharides in the current invention the individual sugar residues are listed from the non-reducing end to the reducing end of the oligosaccharide molecule. The longest sugar chain is chosen as basic chain for the notation. The reducing end of an N- or O-linked oligosaccharide is the monosaccharide residue, which is directly bound to the amino acid of the amino acid backbone of the antibody, whereas the end of an N- or O-linked oligosaccharide, which is located at the opposite terminus as the reducing end of the basic chain, is termed non-reducing end.

All oligosaccharides are described herein with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclatures see, Essentials of Glycobiology Varki et al. eds., 1999, CSHL Press.

The term "defined glycostructure" denotes within this application a glycostructure in which the monosaccharide residue at the non-reducing ends of the glycostructure is of a specific kind. The term "defined glycostructure" denotes within this application a glycostructure in which the monosaccharide residue at the non-reducing end of glycostructures are defined and of a specific kind.

Antibody Purification

The term "affinity chromatography" as used within this application denotes a chromatography method which employs an "affinity chromatography material". In an affinity chromatography antibodies are separated based on their biological activity or chemical structure depending on the formation of electrostatic interactions, hydrophobic bonds, and/or hydrogen bonds to the chromatographical functional groups of the chromatography material. To recover the specifically bound antibody from the affinity chromatography material either a competitor ligand can be added or the chromatography conditions, such as pH value, polarity or ionic strength of the buffer, can be changed. Exemplary "affinity chromatography materials" are metal chelating chromatography materials such as Ni(II)—NTA or Cu(II)—NTA, or antibody affinity chromatography materials such as chromatography materials comprising thereto covalently linked protein A or protein G, or enzyme binding affinity chromatography materials such as chromatography materials comprising thereto covalently bound enzyme substrate analogues, enzyme cofactors, or enzyme inhibitors as chromatographical functional group, or lectin binding chromatography materials such as chromatography materials comprising thereto covalently linked polysaccharides, cell surface receptors, glycoproteins, or intact cells as chromatographical functional group.

In one embodiment the antibody light chain affinity ligand uses a light chain constant domain specific capture reagent, which e.g. specific for the kappa or the lambda constant light chain, depending on whether a kappa or a lambda light chain is contained in the antibody. Examples of such light chain constant domain specific capture reagents are e.g. KappaSelect™ and LambdaFabSelect™ (available from GE Healthcare/BAC), which are based on a highly rigid agarose base matrix that allows high flow rates and low back pressure at large scale. These materials contain a ligand that binds to the constant region of the kappa or the lambda light chain, respectively (antibodies or fragments thereof lacking the constant region of the light chain will not bind). Both are therefore capable of binding other target molecules containing the constant region of the light chain, for example, IgG, IgA and IgM. The ligands are attached to the matrix via a long hydrophilic spacer arm to make them easily available for binding to the target molecule. They are based on a single-chain antibody fragment that is screened for either human Ig kappa or lambda.

The term "light chain" denotes the shorter polypeptide chains of native IgG antibodies. The light chain of an antibody may be assigned to one of two types, called kappa (κ) and lambda (λ), based on the amino acid sequence of its constant domain, see SEQ ID NO: 27 for a human kappa light chain constant domain and SEQ ID NO: 28 for a human lambda light chain constant domain.

The term "applying to" and grammatical equivalents thereof as used within this application denotes a partial step of a purification method in which a solution containing a substance of interest is brought in contact with a stationary phase. The solution containing the substance of interest to be purified passes through the stationary phase providing for an interaction between the stationary phase and the substances in solution. Depending on the conditions, such as e.g. pH, conductivity, salt concentration, temperature, and/or flow rate, some substances of the solution are bound to the stationary phase and therewith are removed from the solution. Other substances remain in solution. The substances remaining in solution can be found in the flow-through. The "flow-through" denotes the solution obtained after the passage of the chromatographic device, which may either be the applied solution containing the substance of interest or the buffer, which is used to flush the column or to cause elution of one or more substances bound to the stationary phase. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance in substantially homogeneous form.

An antibody or antibody fragment whose glycostructure can be modified in the methods as reported herein can be produced by recombinant means. Methods for recombinant production are widely known in the state of the art and comprise protein expression in eukaryotic cells with subsequent isolation of the antibody or antibody fragment and purification to a pharmaceutically acceptable purity. For the expression of the antibody or antibody fragment either a hybridoma cell or a eukaryotic cell, in which one or more nucleic acids encoding the antibody or antibody fragment have been introduced, is used. In one embodiment the eukaryotic cells is selected from CHO cells, NS0 cells, SP2/0 cells, HEK 293 cells, COS cells, PER.C6 cells, BHK cells, rabbit cells, or sheep cells. In another embodiment the eukaryotic cell is selected from CHO cells, HEK cells, or rabbit cells. After expression the antibody or antibody fragment is recovered from the cells (from the supernatant or from the cells after lysis). General methods for recombinant production of antibodies are well-known in the state of the art and reported, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

Purification of antibodies can be performed in order to eliminate cellular components or other contaminants, e.g.

other cellular nucleic acids or proteins, by standard techniques, including alkaline/SDS treatment, CsCl banding, column chromatography, agarose gel electrophoresis, and others well known in the art (see e.g. Ausubel, F. M, et al. (eds.), Current Protocols in Molecular Biology, John Wiley & Sons, Inc., New York (2005)). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis), as well as combinations thereof, such as affinity chromatography with microbial proteins, cation exchange chromatography and anion exchange chromatography (see e.g. Vijayalakshmi, M. A., Appl. Biochem. Biotech. 75 (1998) 93-102). General chromatographic methods and their use are known to a person skilled in the art. See for example, Heftmann, E. (ed.), Chromatography, 5$^{th}$ edition, Part A: Fundamentals and Techniques, Elsevier Science Publishing Company, New York (1992); Deyl, Z. (ed.), Advanced Chromatographic and Electromigration Methods in Biosciences, Elsevier Science BV, Amsterdam, The Netherlands (1998); Poole, C. F., and Poole, S. K., Chromatography Today, Elsevier Science Publishing Company, New York (1991); Scopes, Protein Purification: Principles and Practice (1982); Sambrook, J., et al. (eds.), Molecular Cloning: A Laboratory Manual, Second Edition, Cold Spring Harbor Laboratory Press, Cold Spring Harbor, N.Y. (1989); or Ausubel, F. M., et al. (eds.), Current Protocols in Molecular Biology, John Wiley & Sons, Inc., New York (2005).

For the purification of antibodies or antibody fragments, which have been produced e.g. by cell cultivation methods, generally a combination of different chromatography steps can be employed. Normally a (protein A) affinity chromatography is followed by one or two additional separation steps. In one embodiment the additional chromatography steps are a cation and an anion exchange chromatography step or vice versa. The final purification step is a so called "polishing step" for the removal of trace impurities and contaminants like aggregated immunoglobulins, residual HCP (host cell protein), DNA (host cell nucleic acid), viruses, or endotoxins. In one embodiment the final purification step is an anion exchange chromatography in flow-through mode.

The Method as Reported Herein

The glycostructure of a recombinantly produced antibody or antibody fragment will be determined by the employed cell line and the employed cultivation conditions. With conventional downstream processing techniques selective removal of specific glycostructures is not possible.

In more detail, recombinantly produced monoclonal antibodies generally comprise at glycosylation sites a heterogeneous mixture of glycoforms. This glycosylation profile is influenced by different factors during the recombinant production, such as the enzyme activities present in the host cell as well as in the cultivation medium, and the cultivation conditions.

There is a need to produce an antibody with a prevalent or even pre-determined glycosylation, such as e.g. amongst other things the therapeutic effect.

The method as reported herein provides an antibody with defined glycosylation at an N-glycosylation site, e.g. at an N-glycosylation site in the Fab region or in the Fc-region, i.e. containing essentially a single glycoform attached to the Fc-region glycosylation site, e.g. at Asn297 in the Fc-region, by enzymatically modifying the glycan at the N-glycosylation site following harvesting the antibody from a culture and at the same time allows the enzymes used in the modification to be recycled and re-used for several times. The glycosylation of the antibody can be modified in a desired manner, and as such, the method as reported herein has the advantage that it can be easily incorporated into standard operating procedures used in antibody purification from culture supernatant.

The term "antibody with defined glycosylation" or "antibody with defined glycostructure" denotes a population of antibody molecules wherein a limited number of different glycans are attached to a (predetermined)N-glycosylation site, e.g. in the Fc-region at Asn297 (numbering according to EU index of Kabat). In one embodiment one of the glycans account for 50% or more of the G0F, G1F and G2F glycoforms or for 30% or more of the G0F, G1F, G2F, G1S1F, G2S1F and G2S2F glycoforms.

The term "substantially" as used herein denotes that 40% or more, in one embodiment 50% or more, of the compounds has the same glycosylation, i.e. comprises the same glycan at the N-glycosylation site, e.g. at Asn297 (numbering according to Kabat) in the Fc-region.

With the method as reported herein antibodies, irrespective of type and size, can be modified to comprise a defined glycoform. More specifically, the glycosylation of an N-glycosylation site, e.g. in the Fc-region can be tailor-made, e.g. for the intended therapeutic applications of the antibody. For example, galactosylation of the Fc-region of the antibody is useful for the treatment of cancers. Further for example, sialylation of the Fc-region of an antibody to a defined glycoform is useful in the treatment of autoimmune disorders. For different applications de-galactosylation may be desired and/or de-sialylation of the Fc-region. Still in other embodiments production of hybrid structures having a core of GlcNAc and mannose residues may be effected such as N-acetyl glucosamine, GlcNAc; or mannose-N-acetyl glucosamine-N-acetyl glucosamine, Man-GlcNAc-GlcNAc. Any of the foregoing may be produced using the method as reported herein, as any antibody and any glycostructure of said antibody can be modified stepwise by repeating in a series the method as reported herein with different glycosylation enzymes in order to produce a desired defined glycoform antibody.

For example, an antibody with a G2 glycoform can be produced from a heterogeneous population of monoclonal antibodies using the method as reported herein. The same method can be used to convert non-fucosylated heterogeneous antibodies, which can be produced by glyco-engineering methods, to homogeneous G2-glycoforms. In addition, the batch to batch variability of galactosylation of antibodies can also be addressed by modulating the galactosylation to a desired level using the method as reported herein.

Briefly, the method as reported herein comprises the steps of incubating an antibody with glycosylation at an N-glycosylation site, e.g. in the Fc-region, with one or more glycosylation modifying enzymes. This incubation can be in solution or on-column. The reaction buffer can be further optimized with the addition of selected secondary enzyme (s), optionally cofactor(s) and optionally nucleotide sugar(s). The mixture is then incubated, either at room temperature or at an elevated temperature of about 37° C. The modified antibody and the modifying enzymes are separated thereafter. For example if the modification has been carried out in solution the antibody or the enzyme(s) or both are bound to a chromatographic material and by sequential elution separated from each other.

In one embodiment the method as reported herein comprises the steps of applying a solution comprising an antibody with glycosylation at an N-glycosylation site, e.g. in the Fc-region, to an antibody (light chain or Fc-region) affinity ligand immobilized to a solid phase/support. The support comprises a column that is washed with wash buffer and then with a reaction buffer solution that is suitable for a corresponding desired enzymatic on column glycostructure modification. The reaction buffer can be further optimized with the addition of selected secondary enzyme(s), optionally cofactor(s) and optionally nucleotide sugar(s). The column is then incubated, either at room temperature or at an elevated temperature of about 37° C. The column is thereafter washed with the wash buffer and the modified monoclonal antibody with a defined glycoform is eluted from the solid support using an elution buffer. The eluted antibody may then be neutralized using a neutralization buffer.

In one embodiment the method as reported herein comprises the steps of incubating a solution comprising an antibody with glycosylation at an N-glycosylation site, e.g. in the Fc-region, with one or more glycosylation modifying enzymes in a reaction buffer. The reaction buffer can be further optimized with the addition of selected secondary enzyme(s), optionally cofactor(s) and optionally nucleotide sugar(s). The incubation can be either at room temperature or at an elevated temperature of about 37° C. The antibody and the modifying enzymes are separated thereafter using a chromatography step.

The nucleotide sugars for use in the reaction buffer are selected from the group consisting of UDP-Glc, UDP-Gal, UDP-GalNAc, UDP-GlcNAc, UDP-GlcUA, UDP-Xyl, GDP-Man, GDP-Fuc, CMP-NeuSAc, CMP-NeuSGc and combinations thereof. Concentrations used in the reaction buffer are in the range of about 0.5 mM to about 5 mM, in aspects from about 1 mM to about 1.5 mM. The cofactor for use in the reaction buffer may be selected from the group consisting of $Mn^{2+}$, $Ca^{2+}$, $Mg^{2+}$, $Na^+$, $K^+$, α-Lactalbumin and combinations thereof. Concentrations of cofactor for use in the reaction buffer may be in the range of about 2 mM to about 10 mM.

The antibody (light chain or Fc-region) affinity ligand immobilized on a solid phase that is retained in the column during the purification and modification process. The solid phase includes but is not limited to agarose, sepharose, polyacrylic, polystyrene and other synthetic polymers, which provide negligible non-specific adsorption of non-target proteins and enzymes of modification. The affinity ligand is covalently bound to the solid phase by, for example any of a variety of chemistries, such as N-hydroxysuccinimide (NHS) esters, epoxide, aldehyde, or cyanogen bromide, to a solid phase. Such conjugation chemistries are well-known in the art, as exemplified in Hermanson, G. T., Bioconjugate Techniques, Academic Press (Amsterdam, the Netherlands, Ed. 2008) and Wong, S., Chemistry of Protein Conjugation and CrossLinking, CRC Press (Boca Raton, Fla., 1991).

The wash buffer assures that a high affinity between antibody and affinity ligand during the washing steps is maintained. For example, phosphate buffered saline solution (PBS) with pH of about 7.2 can be used as wash buffer, however it is understood by one of skill in the art that the pH may vary to some degree. The wash and reaction buffers assure that high affinity between antibody and affinity ligand is maintained and, at the same time, the activity of the respective enzyme(s) is maintained. The wash and reaction buffers are used at temperatures of about 25° C. to about 40° C., and any temperature therein between. Temperatures of about 37° C. are often used. The optimum pH range for high affinity of antibodies to the light chain affinity ligand is about 6.0 to about 8.0. Within this range of pH, the buffers overlap with optimum pH ranges of the affinity ligands that can be used in the method as reported herein. These include but are not limited to TRIS buffer, BIS-TRIS buffer, MES buffer, BES buffer, MOPS buffer and HEPES buffer.

Washing conditions for the affinity column minimizes non-specific binding and, thus, affect enzyme reaction and, thus, antibody modification. Wash conditions are such that they will not break the bind between the antibody light chain affinity ligand and the target monoclonal antibody.

Enzymes suitable for use in the methods as reported herein can be selected depending on the modification from the group consisting of mannosyl-glucosamine transferases (MGAT1, MGAT2 and MGAT3); galactosyltransferases (β4GalT1, β4GalT2, β4GalT3, β4GalT4, β4GalT5, β4GalT6, β4GalT7), sialyltransferases (ST6Gal1, ST6Gal2); mannosidases (α mannosidase-I, α mannosidase-II, α(1-2) mannosidase, α(1-6) mannosidase, α(1-2,3) mannosidase, α(1-2,3,6) mannosidase); hexosaminidases (β-N-acetyl hexosaminidase, β-N-acetyl glucosaminidase, α-N-acetyl glucosaminidase); galactosidases (β-galactosidase, β(1-4) galactosidase, α(1-3,6) galactosidase); sialidases (α(2-3,6,8) sialidase, α(2-3) sialidase), fucosidases (α-L-fucosidase, α(1-6) fucosidase, α(1-2) fucosidase, α(1-3,4) fucosidase, α(1-2,3,4) fucosidase) and any combinations thereof.

The method as reported herein can be used to remove or add the terminal sialic acid from galactose for the generation of an antibody with homogeneous G2 glycostructure, e.g. in the Fc-region. Therefore, for example, a non-specific neuraminidase enzyme can be utilized which removes the sialic acid from any linkage or a specific sialidase that add the respective sialic acid. This enzyme can be used in combination with a galactosyltransferase to concomitantly effect galactosylation and removal or addition of sialic acid. Thereby an antibody with a defined G2 glycoform in the Fc-region can be obtained from an antibody with a glycosylation in the Fc-region comprising at least the glycoforms G0, G1, G2, G1S1 and G2S2.

The modification of the glycosylation of an antibody according to the method as reported herein can be performed using a sequential incubation with the individual enzymes, or a semi-sequential incubation, wherein the first enzyme is added and the second enzyme is added after a certain period of time while the first enzyme is not removed, or a simultaneous incubation with both enzyme being present together. Any of these protocols results in an improved modification compared to the modification completely in solution reaction or to the modification with the antibody immobilized on protein A.

The steps of enzymatic modification used in the method as reported herein is exemplified in the following by providing an antibody with defined galactosylation and sialylation in the Fc-region by use of corresponding transferase enzymes.

On-Column Galactosylation

A purified humanized antibody of the IgG1 subclass was applied to protein A affinity chromatography material and an antibody light chain affinity ligand chromatography material (Kappa select from GE Healthcare). The bound antibody was incubated on-column with a buffered solution comprising a galactosyltransferase (GalT1) and UDP-GAL. The results are presented in the following table. It can be seen that a higher amount of galactosylation is achieved when the antibody is bound to a column comprising the antibody light chain affinity ligand.

| | enzymatic modification of Fc-region N-glycosylation performed on an antibody Fc-region affinity ligand chromatography material (protein A) | | | enzymatic modification of Fc-region N-glycosylation performed on an antibody light chain affinity ligand chromatography material (Kappa select) | | |
|---|---|---|---|---|---|---|
| time [h] | G0F [%] | G1F [%] | G2F [%] | G0F [%] | G1F [%] | G2F [%] |
| 0 | 50 | 35 | 15 | 50 | 35 | 15 |
| 2 | 33 | 50 | 17 | 19 | 58 | 23 |
| 7 | 25 | 50 | 25 | 5 | 49 | 46 |
| 24 | 17 | 42 | 41 | 0 | 22 | 78 |

G0F = complex N-glycan with two terminal N-acetyl glucosamine residues and fucose
G1F = complex N-glycan with one terminal N-acetyl glucosamine residue and one terminal galactose residue and fucose
G2F = complex N-glycan with two terminal galactose residues and fucose A purified humanized antibody of the IgG1 subclass with a homogeneous glycosylation in the Fc-region (homogeneous G2F glycoform) was applied to protein A affinity chromatography material and an antibody light chain affinity ligand chromatography material (Kappa select from GE Healthcare). The bound antibody was incubated on-column with a buffered solution comprising a sialyltransferase (ST6) and CMP-NANA. The results are presented in the following table. It can be seen that a higher amount of sialylation is achieved when the antibody is bound to a column comprising the antibody light chain affinity ligand.

| | enzymatic modification of Fc-region N-glycosylation performed on an antibody Fc-region affinity ligand chromatography material (protein A) | | | enzymatic modification of Fc-region N-glycosylation performed on an antibody light chain affinity ligand chromatography material (Kappa select) | | |
|---|---|---|---|---|---|---|
| 37° C. time [h] | G2F [%] | G2S1F [%] | G2S2F [%] | G2F [%] | G2S1F [%] | G2S2F [%] |
| 0 | 100 | 0 | 0 | 100 | 0 | 0 |
| 2 | 17 | 66 | 17 | 0 | 74 | 26 |
| 7 | 11 | 59 | 30 | 0 | 44 | 56 |
| 24 | 10 | 58 | 32 | 0 | 45 | 55 |
| 48 | 12 | 58 | 30 | | | |

| | enzymatic modification of Fc-region N-glycosylation performed on an antibody Fc-region affinity ligand chromatography material (protein A) | | | enzymatic modification of Fc-region N-glycosylation performed on an antibody light chain affinity ligand chromatography material (Kappa select) | | |
|---|---|---|---|---|---|---|
| RT time [h] | G2F [%] | G2S1F [%] | G2S2F [%] | G2F [%] | G2S1F [%] | G2S2F [%] |
| 0 | 100 | 0 | 0 | 100 | 0 | 0 |
| 24 | — | — | — | 0 | 38 | 62 |
| 48 | 15 | 54 | 31 | — | — | — |

The presence or absence of alkaline phosphatase did not change the yield on the protein A column (19% G2F, 56% G2S1F, 25% G2S2F). In solution the following result can be obtained:

| 37° C. | in solution | | |
|---|---|---|---|
| time [h] | G2F [%] | G2S1F [%] | G2S2F [%] |
| 0 | 100 | 0 | 0 |
| 48 | 0 | 40-30 | 60-70 |

G2F = complex N-glycan with two terminal galactose residues and fucose
G2S1F = complex N-glycan with two terminal galactose residues one being sialidated and fucose
G2S2F = complex N-glycan with two terminal galactose residues both being sialidated and fucose A human antibody of the IgG4 subclass was applied to protein A affinity chromatography material and an antibody light chain affinity ligand chromatography material (Kappa select from GE Healthcare). The bound antibody was incubated on-column with a buffered solution comprising a galactosyltransferase (GalT1) and UDP-GAL. The results are presented in the following table. It can be seen that a higher amount of galactosylation is achieved when the antibody is bound to a column comprising the antibody light chain affinity ligand.

| | enzymatic modification of Fc-region N-glycosylation performed on an antibody Fc-region affinity ligand chromatography material (protein A) | | | enzymatic modification of Fc-region N-glycosylation performed on an antibody light chain affinity ligand chromatography material (Kappa select) | | |
|---|---|---|---|---|---|---|
| time [h] | G0F [%] | G1F [%] | G2F [%] | G0F [%] | G1F [%] | G2F [%] |
| 0 | 91 | 9 | 0 | 91 | 9 | 0 |
| 2 | 49 | 36 | 15 | 13 | 49 | 38 |
| 7 | 26 | 33 | 41 | 0 | 14 | 86 |
| 24 | 13 | 22 | 65 | 0 | 0 | 100 |

G0F = complex N-glycan with two terminal N-acetyl glucosamine residues and fucose
G1F = complex N-glycan with one terminal N-acetyl glucosamine residue and one terminal galactose residue and fucose
G2F = complex N-glycan with two terminal galactose residues and fucose A human antibody of the IgG4 subclass with a homogeneous glycosylation in the Fc-region (homogeneous G2F glycoform) was applied to protein A affinity chromatography material and an antibody light chain affinity ligand chromatography material (Kappa select from GE Healthcare). The bound antibody was incubated on-column with a buffered solution comprising a sialyltransferase (ST6) and CMP-NANA. The results are presented in the following table. It can be seen that a higher amount of sialylation is achieved when the antibody is bound to a column comprising the antibody light chain affinity ligand.

| | enzymatic modification of Fc-region N-glycosylation performed on an antibody Fc-region affinity ligand chromatography material (protein A) | | | enzymatic modification of Fc-region N-glycosylation performed on an antibody light chain affinity ligand chromatography material (Kappa select) | | |
|---|---|---|---|---|---|---|
| time [h] | G2F [%] | G2S1F [%] | G2S2F [%] | G2F [%] | G2S1F [%] | G2S2F [%] |
| 0 | 100 | 0 | 0 | 100 | 0 | 0 |
| 7 | n.d. | n.d. | n.d. | 0 | 6 | 94 |
| 24 | 0 | 22 | 78 | 0 | 0 | 100 | n.d. = not determined

A humanized antibody of the IgG1 subclass with an additional glycosylation site in the Fab was applied to protein A affinity chromatography material and an antibody light chain affinity ligand chromatography material (Kappa select from GE Healthcare). The bound antibody was incubated on-column with a buffered solution comprising a sialyltransferase (ST6) and CMP-NANA. The results are presented in the following table. In this example the glycosylation of an N-glycosylation site in the Fab was modified. It can be seen that an improved reaction kinetic is achieved when the antibody is bound to a column comprising the antibody light chain affinity ligand.

| | enzymatic modification of Fab-region N-glycosylation performed on an antibody Fc-region affinity ligand chromatography material (protein A) | | | enzymatic modification of Fab-region N-glycosylation performed on an antibody light chain affinity ligand chromatography material (Kappa select) | | |
|---|---|---|---|---|---|---|
| time [h] | G2 [%] | G2S1 [%] | G2S2 [%] | G2 [%] | G2S1 [%] | G2S2 [%] |
| 0 | 0 | 52 | 48 | 0 | 51 | 49 |
| 2 | 0 | 20 | 80 | 0 | 8 | 92 |
| 7 | 0 | 5 | 95 | 0 | 6 | 94 |
| 24 | 0 | 5 | 95 | 0 | 8 | 92 |

G2 = complex N-glycan with two terminal galactose residues
G2S1 = complex N-glycan with two terminal galactose residues one being sialidated
G2S2 = complex N-glycan with two terminal galactose residues both being sialidated Cell-free cultivation supernatant comprising a humanized antibody of the IgG1 subclass was applied to protein A affinity chromatography material and an antibody light chain affinity ligand chromatography material (Kappa select from GE Healthcare). The bound antibody was incubated on-column sequentially first with a buffered solution comprising a galactosyltransferase (GalT1) and UDP-GAL, and second with a buffered solution comprising a sialyltransferase (ST6) and CMP-NANA. The results are presented in the following table. The sialyltransferase was added after 6 hours incubation time.

| time [h] | G0F [%] | G1F [%] | G2F [%] | G1S1F [%] | G2S1F [%] | G2S2F [%] |
|---|---|---|---|---|---|---|
| | | | protein A | | | |
| 0 | 50 | 38 | 12 | 0 | 0 | 0 |
| 6 | 26 | 47 | 27 | 0 | 0 | 0 |
| 8 | 25 | 36 | 9 | 9 | 14 | 6 |
| 24 | 26 | 31 | 7 | 15 | 13 | 9 |
| 48 | 26 | 32 | 7 | 14 | 13 | 9 |
| | | | Kappa select | | | |
| 0 | 50 | 38 | 12 | 0 | 0 | 0 |
| 6 | 3 | 42 | 55 | 0 | 0 | 0 |
| 8 | 3 | 32 | 8 | 10 | 39 | 8 |
| 24 | 0 | 24 | 6 | 19 | 30 | 21 |
| 48 | 0 | 24 | 6 | 19 | 30 | 21 |

The same experiment was repeated with purified bulk material.

| time [h] | G0F [%] | G1F [%] | G2F [%] | G1S1F [%] | G2S1F [%] | G2S2F [%] |
|---|---|---|---|---|---|---|
| | | | protein A | | | |
| 0 | 52 | 40 | 8 | 0 | 0 | 0 |
| 6 | 26 | 48 | 26 | 0 | 0 | 0 |
| 8 | 25 | 38 | 8 | 9 | 14 | 5 |
| 24 | 27 | 34 | 7 | 8 | 14 | 10 |
| 48 | 25 | 33 | 6 | 14 | 13 | 9 |
| | | | Kappa select | | | |
| 0 | 52 | 40 | 8 | 0 | 0 | 0 |
| 6 | 4 | 46 | 50 | 0 | 0 | 0 |
| 8 | 4 | 36 | 6 | 10 | 36 | 8 |
| 24 | 0 | 28 | 4 | 20 | 29 | 19 |
| 48 | 0 | 28 | 3 | 21 | 29 | 19 |

Improved kappa select method with addition of sialyltransferase after 24 hours

| time [h] | G0F [%] | G1F [%] | G2F [%] | G1S1F [%] | G2S1F [%] | G2S2F [%] |
|---|---|---|---|---|---|---|
| 0 | 52 | 40 | 8 | 0 | 0 | 0 |
| 24 | 0 | 22 | 78 | 0 | 0 | 0 |
| 30 | 0 | 12 | 0 | 6 | 53 | 29 |

Enzyme Recycling when Used On-Column

A recombinant humanized antibody of the IgG1 subclass was applied to an affinity chromatography material under conditions wherein the antibody was bound to said material. The bound antibody was incubated on-column with a buffered solution comprising a galactosyltransferase (GalT1) and UDP-GAL. This solution was after the incubation recovered and re-conditioned by concentration and buffer exchanger a further enzymatic modification reaction. The results are presented in the following table (24h time point).

| use cycle | G0F [%] | G1F [%] | G2F [%] |
|---|---|---|---|
| reference | 0 | 0 | 100 |
| after first use | 0 | 0 | 100 |
| after second use | 0 | 48 | 52 |

It can be seen that the galactosyltransferase can be re-used once without loss of enzymatic conversion efficiency and a second time with a loss of enzymatic conversion efficiency of about 50%.

A recombinant humanized antibody of the IgG1 subclass was applied to an affinity chromatography material under conditions wherein the antibody was bound to said material. The bound antibody was incubated on-column with a buffered solution comprising a sialyltransferase (ST6) and CMP-NANA. This solution was recovered and re-conditioned after the incubation by concentration and buffer exchange for a further enzymatic modification reaction. The results are presented in the following table (6h time point).

enzyme concentration 4 mg/ml

| use cycle | G2S1F [%] | G2S2F [%] |
|---|---|---|
| reference | 32 | 68 |
| after first use | 23 | 77 |
| after second use | 24 | 76 | enzyme concentration 1 mg/ml

| use cycle | G2S1F [%] | G2S2F [%] |
|---|---|---|
| reference | 34 | 66 |
| after third use | 32 | 68 |

It can be seen that the sialyltransferase can be re-used for at least three times without loss of enzymatic conversion efficiency.

Enzyme Recycling when Used in Solution

Co-Incubation with GalT and ST6

In a reaction buffer comprising UDP-GAL and CMP-NANA a humanized antibody of the IgG1 subclass, a galactosyltransferase (GalT1) and, a sialyltransferase (ST6) were co-incubated. Thereafter the enzymatically modified antibody and the enzymes were separated using a cation exchange chromatography (S-sepharose). The specific enzymatic activities of the recovered enzymes were determined after each use cycle. The results are presented in the following table.

| use cycle | 1 | 2 | 3 |
|---|---|---|---|
| GalT | 11.8 U/mg | 8.5 U/mg | 12.1 U/mg |
| ST6 | 742 U/µg | 676 U/µg | 703 U/µg | reaction conditions: 25 mg antibody, 2.5 mg GalT, 2.5 mg ST6, 50 mM MES, pH 6.4, 10 ml reaction volume
S-Sepharose chromatography conditions: 0.5 × 10 cm S-Sepharose column; wash with 20 column volumes 40 mM TRIS pH 7.4 Tris-HCl resulted in elution of GalT; elution of antibody with step to 30 mM MES, 95 mM NaCl, pH 5.6; elution of ST6 with linear gradient to 50 mM MES, pH 6.4, 1M NaCl An SDS-page gel analysis showed no degradation or aggregation products of GalT or ST6 and good separation (see FIG. 1).

GalT, the modified antibody and ST6 could be separated on the cation exchange column.

Incubation with GalT

In a reaction buffer comprising UDP-GAL a humanized antibody of the IgG1 subclass and a galactosyltransferase (GalT1) were co-incubated. Thereafter the enzymatically modified antibody and the enzyme were separated using a cation exchange chromatography (S-sepharose). The galactosyltransferase was reused three times. The results are presented in the following table.

| | first use | | | three times re-used | | |
|---|---|---|---|---|---|---|
| time [h] | G0F [%] | G1F [%] | G2F [%] | G0F [%] | G1F [%] | G2F [%] |
| 0 | 50 | 35 | 15 | 50 | 35 | 15 |
| 6.5 | 0 | 15 | 85 | 0 | 17 | 83 |
| 24 | 0 | 0 | 100 | 0 | 0 | 100 |

Incubation with ST6

In a reaction buffer comprising CMP-NANA a humanized antibody of the IgG1 subclass and a sialyltransferase (ST6) were co-incubated. Thereafter the enzymatically modified antibody and the enzyme were separated using a cation exchange chromatography (S-sepharose). The sialyltransferase was re-used three times. The results are presented in the following table.

| | first use | | | three times re-used | | |
|---|---|---|---|---|---|---|
| time [h] | G2F [%] | G2S1F [%] | G2S2F [%] | G2F [%] | G2S1F [%] | G2S2F [%] |
| 6.5 | 0 | 31 | 69 | 0 | 39 | 61 |
| 24 | 0 | 32 | 69 | 0 | 40 | 61 |

The Antibody Used in the Methods as Reported Herein

Chimeric and Humanized Antibodies

In certain embodiments, an antibody modified in the method as reported herein is a chimeric antibody.

Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof as long as these bind to the antibody light chain affinity ligand used in the method as reported herein.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005)

43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

Human Antibodies

In certain embodiments, an antibody modified in the method as reported herein is a human antibody.

Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, US 2007/0061900, describing VELOCIMOUSE® technology, and WO 2007/131676 describing an immunoreconstituted mouse). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95). Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies modified in the method as reported herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

Multispecific Antibodies

In certain embodiments, an antibody modified in the method as reported herein is a multispecific antibody, e.g. a bispecific antibody. Multispecific antibodies are monoclonal antibodies that have binding specificities for at least two different sites. Bispecific antibodies can be prepared as full length antibodies or antibody fragments. Fragments of multispecific (bispecific) antibodies are encompassed as long as these bind to the antibody light chain affinity ligand as used in the methods as reported herein.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tuft, A. et al., J. Immunol. 147 (1991) 60-69).

Engineered antibodies with three or more functional antigen binding sites, including "Octopus antibodies," are also included herein (see, e.g. US 2006/0025576).

The antibody or fragment modified in the method as reported herein also includes a "Dual Acting Fab" or "DAF" (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the second light chain comprising the first heteromonomeric Fc-region polypeptide, one for the second light chain, and one for the second heavy chain comprising the second heteromonomeric Fc-region polypeptide. For example, one of the heterodimeric heavy chain comprises to so-called "knobs mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73). Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs and T-cell bispecific antibodies (see, e.g. Schaefer, W. et al, Proc. Natl. Acad. Sci. USA, 108 (2011) 11187-1191).

In one embodiment isolated nucleic acids encoding an antibody as used in the methods as reported herein are provided.

In a further embodiment, one or more vectors (e.g., expression vectors) comprising such nucleic acid(s) are provided.

In a further embodiment, a host cell comprising such nucleic acid(s) is provided.

In one such embodiment, a host cell comprises (e.g., has been transformed with):

in case of a native antibody or native antibody fragment:
  (1) a vector comprising a nucleic acid that encodes an amino acid sequence comprising the VL of the antibody and an amino acid sequence comprising the VH of the antibody, or
  (2) a first vector comprising a nucleic acid that encodes an amino acid sequence comprising the VL of the antibody and a second vector comprising a nucleic acid that encodes an amino acid sequence comprising the VH of the antibody.

in case of a bispecific antibody with heterodimeric heavy chains:
  (1) a first vector comprising a first pair of nucleic acids that encode amino acid sequences one of them comprising the first VL and the other comprising the first VH of the antibody and a second vector comprising a second pair of nucleic acids that encode amino acid sequences one of them comprising the second VL and the other comprising the second VH of the antibody, or
  (2) a first vector comprising a first nucleic acid that encode an amino acid sequence comprising one of the variable domains (preferably a light chain variable domain), a second vector comprising a pair of nucleic acids that encode amino acid sequences one of them comprising a light chain variable domain and the other comprising the first heavy chain variable domain, and a third vector comprising a pair of nucleic acids that encode amino acid sequences one of them comprising the respective other light chain variable domain as in the second vector and the other comprising the second heavy chain variable domain, or
  (3) a first vector comprising a nucleic acid that encodes an amino acid sequence comprising the first VL of the antibody, a second vector comprising a nucleic acid that encodes an amino acid sequence comprising the first VH of the antibody, a third vector comprising a nucleic acid that encodes an amino acid sequence comprising the second VL of the antibody, and a fourth vector comprising a nucleic acid that encodes an amino acid sequence comprising the second VH of the antibody.

In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising nucleic acids encoding the antibody, as provided above, under conditions suitable for expression of the antibody, optionally recovering the antibody from the host cell (or host cell culture medium), and modifying the glycosylation of the antibody with a method as reported herein.

For recombinant production of an antibody, nucleic acids encoding an antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

Pharmaceutical Formulations

Pharmaceutical formulations of an antibody modified with any of the methods as reported herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Therapeutic Methods and Compositions

Any of the antibodies modified with any of the methods as reported herein may be used in therapeutic methods.

In one aspect, an antibody modified with any of the methods as reported herein for use as a medicament is provided. In further aspects, an antibody modified with any of the methods as reported herein for use in treating a disease is provided. In certain embodiments, an antibody modified with any of the methods as reported herein for use in a method of treatment is provided. In certain embodiments, the invention provides an antibody modified with any of the methods as reported herein for use in a method of treating an individual having a disease comprising administering to the individual an effective amount of the antibody modified with any of the methods as reported herein. In one such embodiment, the method further comprises administering to the individual an effective amount of at least one additional therapeutic agent. In certain embodiments, the invention provides an antibody modified with any of the methods as reported herein for use in a method of treatment in an individual comprising administering to the individual an effective of the antibody modified with any of the methods as reported herein. An "individual" according to any of the above embodiments is preferably a human In a further aspect, the invention provides for the use of an antibody modified with any of the methods as reported herein in the manufacture or preparation of a medicament. In one embodiment, the medicament is for treatment of a disease. In a further embodiment, the medicament is for use in a method of treating a disease comprising administering to an individual having the disease an effective amount of the medicament. In one such embodiment, the method further comprises administering to the individual an effective amount of at least one additional therapeutic agent. In a further embodiment, the medicament is for use in a method of treatment in an individual comprising administering to the individual an amount effective of the medicament. An "individual" according to any of the above embodiments may be a human.

In a further aspect, the invention provides a method for treating a disease. In one embodiment, the method comprises administering to an individual having such a disease an effective amount of an antibody modified with any of the methods as reported herein. In one such embodiment, the method further comprises administering to the individual an effective amount of at least one additional therapeutic agent. An "individual" according to any of the above embodiments may be a human In a further aspect, the invention provides pharmaceutical formulations comprising any of the antibodies modified with any of the methods as reported herein, e.g., for use in any of the above therapeutic methods. In one embodiment, a pharmaceutical formulation comprises any of the antibodies modified with any of the methods as reported herein and a pharmaceutically acceptable carrier. In another embodiment, a pharmaceutical formulation comprises any of the antibodies modified with any of the methods as reported herein and at least one additional therapeutic agent.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody modified with any of the methods as reported herein can occur prior to, simultaneously, and/or following, administration of the additional therapeutic agent or agents. In one embodiment, administration of the antibody modified with any of the methods as reported herein and administration of an additional therapeutic agent occur within about one month, or within about one, two or three weeks, or within about one, two, three, four, five, or six days, of each other. Antibodies modified with any of the methods as reported herein can also be used in combination with radiation therapy.

An antibody modified with any of the methods as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies modified with any of the methods as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody modified with any of the methods as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient.

Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The disclosures of each and every patent, patent application, and publication cited herein are hereby incorporated herein by reference in their entirety.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1 SDS-page of the eluted fractions of the S-Sepharose separation as reported herein and according to Example 5.

EXAMPLES

GalT reaction solution (5 mM MnCl2, 10 mM UDP-Gal, 100 mM MES, 0.05 mg/ml GalT, pH 6.5):
  153 mg UDP-Gal (MW=610.27 g/mol)
  32 mg MnCl2 (MW=125.84 g/mol)
  single use: 460 µGalT (c=5.43 mg/mL; 10 µg/2 mg antibody -> 10 µg in 300 µL=0.033 mg/ml)
  multiple use: 460 µL GalT (c=5.43 mg/mL; 15 µg/1 mg AK -> 15 µg in 300 µL=0.05 mg/mL)
  in 100 mM MES buffer pH 6.5

ST6 reaction solution (0.1 mM ZnCl2, 200 nM AP, 50 mM MES, 1.7 mg/ml CMP-NANA, 0.7 mg/ml ST6, pH 6.5):
  50 µL ZnCl (100 mM solution: 13.6 mg in 1 mL 50 mM MES)
  28 µL alkaline phosphatase (AP) (c=20 mg/mL, MW=56,000 g/mol)
  single use: 167 mg CMP-NANA (1000 µg/2 mg antibody -> 1000 µg pro 300 µL=3.34 mg/mL)
  multiple use: 83.5 mg CMP-NANA (500 µg/1 mg AK -> 500 µg pro 300 µL=1.67 mg/mL)
  single use: 6 mL ST6 (c=5.45 mg/mL, target: 200 µg in 300 µL (2 mg AK)=0.67 mg/mL)
  multiple use: 6 mL ST6 (c=5.45 mg/mL, target: 200 µg in 300 µL (1 mg AK)=0.67 mg/mL)
  in 50 mM MES buffer pH 6.5

Buffers:
  Regeneration buffer 1 (0.1 M phosphoric acid)
  Regeneration buffer 2 (3 M Guanidine-HCl)
  Equilibration buffer (25 mM Tris, 25 mM NaCl, 5 mM EDTA, pH7.1)
  Wash buffer 1 (100 mM MES, pH 6.5): 21.3 mg MES in 1000 mL H2O, pH 6.5 (adjusted with 50% (w/v) NaOH)
  Wash buffer 2 (1 M Tris, pH 7.2)
  Wash buffer 3 (50 mM MES, pH 6.5): Wash buffer 100 mM MES 1:1 with distilled H2O
  Elution buffer Kappa select (0.1 M glycine, pH 2.7): 750 mg glycine in 100 mL H2O, pH 2.7 (adjusted with 25% (w/v) HCl)
  Elution buffer protein A (25 mM Na-citrate, pH 2.8)

Example 1

Galactosylation of Bulk Material on Column
  regenerate, equilibrate and wash protein A respectively Kappa select columns by applying 2 column volumes regeneration buffer 1, 10 column volumes equilibration buffer and 4 column volumes wash buffer 1
  apply 2 mg of IgG (bulk material) onto the column
  wash with 10 column volumes wash buffer 1
  apply 2 mL galactosylation reaction solution (with 0.033 mg/ml GalT), let 0.8 mL flow through
  incubate respectively at 25° C. (2, 7 or 24 h)
  wash with 8 column volumes wash buffer 1
  elute with the respective elution buffer (2 column volumes for Protein A; 8 column volumes for kappa select) and use 1 M Tris buffer (pH 9.0) for pH adjustment Example 2

Sialylation of IgG1 Bulk Material on Column (Protein A)
  regenerate, equilibrate and wash protein A resp, kappa select columns by applying 2 column volumes regeneration buffer 1, 10 column volumes equilibration buffer and 10 column volumes wash buffer 3
  apply 2 mg of IgG (bulk material) onto the column
  apply 2 mL sialylation reaction solution (3.3 mg/ml instead of 1.7 mg/ml CMP-NANA, +/−AP), let 0.8 mL flow through
  incubate respectively at 37° C. (2, 7, 24 or 48 hours) and 25° C. (48 h)
  wash with 4 column volumes wash buffer 3
  elute with 2 column volumes of Elution buffer (sodium citrate) and use 1 M Tris buffer (pH 9.0) for pH adjustment Sialylation of IgG1 Bulk Material on Column (Kappa Select)
  regenerate, equilibrate and wash Protein A resp, kappa Select columns by applying 2 column volumes equilibration buffer, 3 column volumes regeneration buffer 2, 4 column volumes equilibration buffer and 2 column volumes wash buffer 3
  apply 2 mg of IgG (bulk material) onto the column
  wash with 3 column volumes wash buffer 3
  apply 2 mL sialylation reaction solution (3.3 mg/ml CMP-NANA, +/−AP), let 0.8 mL flow through
  incubate respectively at 37° C. (2, 7, and 24 h) and at 25° C. (24 h)
  wash with 3 column volumes wash buffer 3
  elute with 8 column volumes of Elution buffer Kappa select and use 1 M Tris buffer (pH 9.0) for pH adjustment Example 3

Sequential Galactosylation and Sialylation of Cell Culture Supernatant
  regenerate and equilibrate protein A respectively Kappa select columns by applying 2 column volumes regeneration buffer 1, 10 column volumes equilibration buffer
  apply 1 mg of IgG (in supernatant) onto the column
  wash with 10 column volumes equilibration buffer, then 2 column volumes wash buffer 2 and 6 column volumes wash buffer 1 apply 2 mL galactosylation reaction solution, let 0.8 mL flow through incubate at 25° C. for about 6 to 24 h (to allow for sufficient galactosylation)

wash with 8 column volumes wash buffer 1, 10 column volumes equilibration buffer, 2 column volumes wash buffer 2 and 6 column volumes wash buffer 3 apply 2 mL sialylation reaction solution, let 0.8 mL flow through incubate (e.g. 25° C. respectively for 2, 7 or 24 h or even longer)

wash with 8 column volumes wash buffer 1 elute with the respective elution buffer (2 column volumes for Protein A; 8 column volumes for Kappa select) and use 1 M Tris buffer (pH 9.0) for pH adjustment Example 4

Sequential Galactosylation and Sialylation of Bulk Material regenerate, equilibrate and wash protein A respectively Kappa select columns by applying 2 column volumes regeneration buffer 1, 10 column volumes equilibration buffer and 4 column volumes wash buffer 1 apply 1 mg of IgG (bulk material) onto the column wash with 10 column volumes wash buffer 1 apply 2 mL galactosylation reaction solution, let 0.8 mL flow through incubate at 25° C. for about 6 to 24 h (to allow for sufficient galactosylation)

wash with 8 column volumes wash buffer 1, 10 column volumes equilibration buffer, 2 column volumes wash buffer 2 and 6 column volumes wash buffer 3 apply 2 mL sialylation reaction solution, let 0.8 mL flow through incubate (e.g. 25° C. respectively for 2, 7 or 24 h or even longer)

wash with 8 column volumes wash buffer 1 elute with the respective elution buffer (2 column volumes for protein A; 8 column volumes for Kappa select) and use 1 M Tris buffer (pH 9.0) for pH adjustment Example 5

In Solution Galactosylation and Sialylation with Enzyme Recovery incubation of 25 mg antibody, 2.5 mg galactosyltransferase and 2.5 mg sialyltransferase in 10 mL 50 mM MES buffer pH 6.4 after reaction application of reaction solution to an S-Sepharose column (0.5×10 cm) equilibrated with 50 mM MES pH 6.4 washing with 5 column volumes of 50 mM MES pH 6.4 to remove unbound material washing of column with 20 column volumes 40 mM Tris buffer pH 7.4 and thereby eluting the galactosyltransferase re-equilibrated with 50 mM MES pH 6.4 eluting the antibody with a buffered solution comprising 30 mM MES pH 5.6 and 95 mM NaCl (40 column volumes)

eluting the sialyltransferase with a linear gradient over 10 column volumes to 50 mM MES pH 6.4 and 1 M NaCl fractions containing the target enzymes or the humanized antibody were pooled and concentrated using ultrafiltration devices (Amicon Ultra-15, 10 kDa)

Example 6

Enzyme Re-Use Testing galactosyltransferase: incubation of 500 µg antibody in 78.5 µL reaction buffer (100 mM MES, 10 mM UDP-Gal, 5 mM MnCl2, pH 6.5) with 2.5 galactosyltransferase at 37° C. for a defined time period, e.g. 6.5 h or 24 h sialyltransferase: incubation of 500 µg antibody in 61.8 µl water, 250 µg CMP-NANA dissolved in water, 50 µg sialyltransferase, 200 nM alkaline phosphatase, 0.1 mM ZnCl2 at 37° C. for a defined time period, e.g. 6.5 or 24 hours analysis of the galactosylation by qTOE-ESMS: denaturation and reduction of the sample (approx. 250 µg antibody, 4 M guanidinium, TCEP); buffer exchange to 20% acetonitrile with 1% formic acid; ESMS analytics

What is claimed is:

1. A method for the enzymatic production of an antibody with a modified glycosylation at an N-glycosylation site, comprising the following steps:
   a) incubating a first batch of an antibody that has a glycosylation at an N-glycosylation site with one or more enzymes for a time sufficient and under conditions suitable to modify the glycosylation at the N-glycosylation site to a defined form,
   b) separating in one or more chromatography steps the first batch of the antibody with a modified glycosylation at the N-glycosylation site from the one or more enzymes and thereby i) producing the antibody with a modified glycosylation at the N-glycosylation site and ii) obtaining one or more recycled enzymes, and
   c) incubating a second batch of the antibody in the same production process that has a glycosylation at an N-glycosylation site with the one or more recycled enzymes of step b) for a time sufficient and under conditions suitable to modify the glycosylation at the N-glycosylation site to a defined form.

2. The method according to claim 1, wherein the incubating is either in solution or with the antibody bound to an antibody affinity ligand.

3. The method of claim 2, wherein the antibody affinity ligand is an antibody light chain or Fc-region affinity ligand.

4. The method according to claim 1, wherein in step b) the separating of the first batch of the antibody with a modified glycosylation at the N-glycosylation site from the one or more enzymes is by a cation exchange chromatography.

5. The method according to claim 4, wherein the cation exchange chromatography comprises the following steps:
   i) applying a solution comprising at least one of a galactosyltransferase or a sialyltransferase and the antibody with the modified glycosylation at the N-glycosylation site to a cation exchange chromatography material,
   ii) optionally washing the cation exchange chromatography material to remove unbound compounds from the cation exchange chromatography material but without eluting the antibody with the modified glycosylation at the N-glycosylation site,
   iii) applying a first solution to the cation exchange chromatography material and thereby eluting the galactosyltransferase, if present, from the cation exchange chromatography material,
   iv) applying a second solution to the cation exchange chromatography material and thereby eluting the antibody with the modified glycosylation at the N-glycosylation site from the cation exchange chromatography material, and
   v) applying a linear gradient to the cation exchange chromatography material and thereby eluting the sialyltransferase, if present, from the cation exchange chromatography material.

6. The method according to claim 5, wherein
the solution of step i) is a 2-(N-morpholino) ethanesulfonic acid (MES) buffered solution with a pH value from pH 5.0 to pH 6.5,
the solution of step ii) is a 2-(N-morpholino) ethanesulfonic acid (MES) buffered solution with a pH value from pH 5.0 to pH 6.5,
the solution of step iii) is a tris (hydroxymethyl) aminomethane (TRIS) buffered solution with a pH value from pH 6.6 to pH 8.0,
the solution of step iv) is a 2-(N-morpholino) ethanesulfonic acid (MES) buffered solution with a pH value from pH 5.0 to pH 6.5 comprising about 75 mM to about 125 mM sodium chloride (NaCl), and
the linear gradient is from the solution of step iv) to a 2-(N-morpholino) ethanesulfonic acid (MES) buffered solution with a pH value from pH 5.0 to pH 6.5 comprising about 750 mM to about 1250 mM sodium chloride (NaCl).

7. The method according to claim 4, wherein the cation exchange chromatography material has a matrix of cross-linked agarose with sulfopropyl cation exchange groups.

8. The method according to claim 1, wherein the one or more enzymes is at least one of a galactosyltransferase or a sialyltransferase.

9. The method according to claim 8, wherein the galactosyltransferase is β4GalT1.

10. The method according to claim 8, wherein the sialyltransferase is ST6.

11. The method according to claim 1, wherein the antibody that has a glycosylation at an N-glycosylation site is a bivalent monospecific antibody or a bivalent bispecific antibody or an antibody Fab fragment.

12. The method according to claim 1, wherein the antibody that has a glycosylation at an N-glycosylation site is a chimeric or humanized or human antibody.

13. The method according to claim 1, wherein the antibody that has a glycosylation at an N-glycosylation site is a monoclonal antibody.

14. The method according to claim1, wherein the antibody that has a glycosylation at an N-glycosylation site is an antibody of the human IgG1 or IgG4 subclass.

15. The method according to claim 1, wherein the N-glycosylation site is a Fab region N-glycosylation site or the Fc-region N-glycosylation site at asparagine residue 297 (numbering according to Kabat).

16. The method according to claim 1, wherein the step of incubating includes incubating with one or more activated sugar residues with the one or more enzymes.

17. A method to produce a glycosylation modified antibody comprising:
a) incubating a first batch of an antibody that has a glycosylation at an N-glycosylation site with one or more enzymes for a time sufficient and under conditions suitable to modify the glycosylation at the N-glycosylation site to a defined form,
b) separating in a cation exchange chromatography step the first batch of the modified antibody from the one or more enzymes and thereby i) producing the modified antibody and ii) obtaining one or more recycled enzymes, and
c) incubating a second batch of the antibody in the same production process that has a glycosylation at an N-glycosylation site with the one or more recycled enzymes of step b) for a time sufficient and under conditions suitable to modify the glycosylation at the N-glycosylation site to a defined form.

18. The method according to claim 17, wherein the one or more enzymes is at least one of a galactosyltransferase or a sialyltransferase.

19. The method according to claim 1 or claim 17 further comprising the following steps:
d) separating in one or more chromatography steps the second batch of the antibody with a modified glycosylation at the N-glycosylation site from the one or more recycled enzymes and thereby i) producing the antibody with a modified glycosylation at the N-glycosylation site and ii) obtaining one or more recycled enzymes, and
e) incubating a third batch of the antibody in the same production process that has a glycosylation at an N-glycosylation site with the one or more recycled enzymes of step d) for a time sufficient and under conditions suitable to modify the glycosylation at the N-glycosylation site to a defined form.

* * * * *

SEQUENCE LISTING

<160> NUMBER OF SEQ ID NOS: 28

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 326
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 4
<211> LENGTH: 377
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220
```

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 5
<211> LENGTH: 327
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
                    210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Gln Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 6
<211> LENGTH: 221
<212> TYPE: PRT
<213> ORGANISM: Homo sapiens
<220> FEATURE:
<221> NAME/KEY: MISC_FEATURE
<222> LOCATION: (131)..(131)
<223> OTHER INFORMATION: X=E or D
<220> FEATURE:
<221> NAME/KEY: MISC_FEATURE
<222> LOCATION: (133)..(133)
<223> OTHER INFORMATION: X=M or L

<400> SEQUENCE: 6

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Arg Xaa Glu Xaa Thr Lys Asn Gln Val Ser Leu Thr Cys Leu Val
                130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu His
                195                 200                 205

Asn His Tyr Thr Gln Lys Ser Leu Ser Leu Ser Pro Gly
```

<210> SEQ ID NO 7
<211> LENGTH: 221
<212> TYPE: PRT
<213> ORGANISM: Artificial Sequence
<220> FEATURE:
<223> OTHER INFORMATION: variant human Fc-region of the IgG1 isotype
    with a hole mutation

<400> SEQUENCE: 7

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220
```

<210> SEQ ID NO 8
<211> LENGTH: 221
<212> TYPE: PRT
<213> ORGANISM: Artificial Sequence
<220> FEATURE:
<223> OTHER INFORMATION: variant human Fc-region of the IgG1 isotype
    with a knob mutation

<400> SEQUENCE: 8

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
```

```
                65                  70                  75                  80
Leu Thr Val Leu His Gln Asp Trp Leu Asn Gly Lys Glu Tyr Lys Cys
                    85                  90                  95

Lys Val Ser Asn Lys Ala Leu Pro Ala Pro Ile Glu Lys Thr Ile Ser
                    100                 105                 110

Lys Ala Lys Gly Gln Pro Arg Glu Pro Gln Val Tyr Thr Leu Pro Pro
                    115                 120                 125

Ser Arg Asp Glu Leu Thr Lys Asn Gln Val Ser Leu Trp Cys Leu Val
                    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Val Leu Asp Ser Asp
                    165                 170                 175

Gly Ser Phe Phe Leu Tyr Ser Lys Leu Thr Val Asp Lys Ser Arg Trp
                    180                 185                 190

Gln Gln Gly Asn Val Phe Ser Cys Ser Val Met His Glu Ala Leu His
                    195                 200                 205

Asn His Tyr Thr Gln Lys Ser Leu Ser Leu Ser Pro Gly
                    210                 215                 220
```

<210> SEQ ID NO 9
<211> LENGTH: 221
<212> TYPE: PRT
<213> ORGANISM: Artificial Sequence
<220> FEATURE:
<223> OTHER INFORMATION: variant human Fc-region of the IgG1 isotype
      with the mutations L234A, L235A

<400> SEQUENCE: 9

```
Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                    85                  90                  95

Lys Val Ser Asn Lys Ala Leu Pro Ala Pro Ile Glu Lys Thr Ile Ser
                    100                 105                 110

Lys Ala Lys Gly Gln Pro Arg Glu Pro Gln Val Tyr Thr Leu Pro Pro
                    115                 120                 125

Ser Arg Asp Glu Leu Thr Lys Asn Gln Val Ser Leu Thr Cys Leu Val
                    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                    165                 170                 175

Gly Ser Phe Phe Leu Tyr Ser Lys Leu Thr Val Asp Lys Ser Arg Trp
                    180                 185                 190

Gln Gln Gly Asn Val Phe Ser Cys Ser Val Met His Glu Ala Leu His
                    195                 200                 205
```

Asn His Tyr Thr Gln Lys Ser Leu Ser Leu Ser Pro Gly
        210                 215                 220

<210> SEQ ID NO 10
<211> LENGTH: 221
<212> TYPE: PRT
<213> ORGANISM: Artificial Sequence
<220> FEATURE:
<223> OTHER INFORMATION: variant human Fc-region of the IgG1 isotype
      with a L234A, L235A and hole mutation

<400> SEQUENCE: 10

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
        210                 215                 220

<210> SEQ ID NO 11
<211> LENGTH: 221
<212> TYPE: PRT
<213> ORGANISM: Artificial Sequence
<220> FEATURE:
<223> OTHER INFORMATION: variant human Fc-region of the IgG1 isotype
      with a L234A, L235A and knob mutation

<400> SEQUENCE: 11

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

```
Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Trp Cys Leu Val
            130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly
            210                 215                 220

<210> SEQ ID NO 12
<211> LENGTH: 221
<212> TYPE: PRT
<213> ORGANISM: Artificial Sequence
<220> FEATURE:
<223> OTHER INFORMATION: variant human Fc-region of the IgG1 isotype
      with a L234A, L235A and P329G mutation

<400> SEQUENCE: 12

Cys Pro Pro Cys Pro Ala Pro Glu Ala Ala Gly Gly Pro Ser Val Phe
 1               5                  10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
            50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Gly Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
            130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205
```

Asn His Tyr Thr Gln Lys Ser Leu Ser Leu Ser Pro Gly
        210                 215                 220

<210> SEQ ID NO 13
<211> LENGTH: 226
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and hole mutation

<400> SEQUENCE: 13

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 14
<211> LENGTH: 226
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and knob mutation

<400> SEQUENCE: 14

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

-continued

```
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Gly Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Ser Arg Asp Glu Leu Thr Lys Asn Gln Val Ser
     130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 15
<211> LENGTH: 221
<212> TYPE: PRT
<213> ORGANISM: Artificial Sequence
<220> FEATURE:
<223> OTHER INFORMATION: variant human Fc-region of the IgG1 subclass
      with the mutations L234A, L235A, P329G, Y349C, T366S, L368A and
      Y407V

<400> SEQUENCE: 15

Cys Pro Pro Cys Pro Ala Pro Glu Ala Ala Gly Gly Pro Ser Val Phe
  1               5                  10                  15

Leu Phe Pro Pro Lys Pro Lys Asp Thr Leu Met Ile Ser Arg Thr Pro
                 20                  25                  30

Glu Val Thr Cys Val Val Val Asp Val Ser His Glu Asp Pro Glu Val
             35                  40                  45

Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Gly Ala Pro Ile Glu Lys Thr Ile Ser
             100                 105                 110

Lys Ala Lys Gly Gln Pro Arg Glu Pro Gln Val Cys Thr Leu Pro Pro
         115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160
```

```
Gln Pro Glu Asn Asn Tyr Lys Thr Thr Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220

<210> SEQ ID NO 16
<211> LENGTH: 221
<212> TYPE: PRT
<213> ORGANISM: Artificial Sequence
<220> FEATURE:
<223> OTHER INFORMATION: variant human Fc-region of the IgG1 subclass
      with a L234A, L235A, P329G and S354C, T366W mutation

<400> SEQUENCE: 16

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Gly Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Cys Arg Asp Glu Leu Thr Lys Asn Gln Val Ser Leu Trp Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220

<210> SEQ ID NO 17
<211> LENGTH: 221
<212> TYPE: PRT
<213> ORGANISM: Artificial Sequence
<220> FEATURE:
<223> OTHER INFORMATION: variant human Fc-region of the IgG1 subclass
      with a L234A, L235A, P329G and S354C, T366S, L368A and Y407V
      mutation

<400> SEQUENCE: 17

Cys Pro Pro Cys Pro Ala Pro Glu Ala Ala Gly Gly Pro Ser Val Phe
1               5                   10                  15
```

```
Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Gly Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Cys Arg Asp Glu Leu Thr Lys Asn Gln Val Ser Leu Ser Cys Ala Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220

<210> SEQ ID NO 18
<211> LENGTH: 221
<212> TYPE: PRT
<213> ORGANISM: Artificial Sequence
<220> FEATURE:
<223> OTHER INFORMATION: variant human Fc-region of the IgG1 subclass
      with a L234A, L235A, P329G and Y349C, T366W mutation

<400> SEQUENCE: 18

Cys Pro Pro Cys Pro Ala Pro Glu Ala Ala Gly Gly Pro Ser Val Phe
1               5                  10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Gly Ala Pro Ile Glu Lys Thr Ile Ser
                100                 105                 110

Lys Ala Lys Gly Gln Pro Arg Glu Pro Gln Val Cys Thr Leu Pro Pro
            115                 120                 125

Ser Arg Asp Glu Leu Thr Lys Asn Gln Val Ser Leu Trp Cys Leu Val
130                 135                 140

Lys Gly Phe Tyr Pro Ser Asp Ile Ala Val Glu Trp Glu Ser Asn Gly
```

```
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
                180                 185                 190
Gln Gln Gly Asn Val Phe Ser Cys Ser Val Met His Glu Ala Leu His
                195                 200                 205
Asn His Tyr Thr Gln Lys Ser Leu Ser Leu Ser Pro Gly
                210                 215                 220

<210> SEQ ID NO 19
<211> LENGTH: 221
<212> TYPE: PRT
<213> ORGANISM: Artificial Sequence
<220> FEATURE:
<223> OTHER INFORMATION: variant human Fc-region of the IgG1 subclass
      with the mutations I253A, H310A and H435A

<400> SEQUENCE: 19

Cys Pro Pro Cys Pro Ala Pro Glu Leu Leu Gly Gly Pro Ser Val Phe
1               5                   10                  15
Leu Phe Pro Pro Lys Pro Lys Asp Thr Leu Met Ala Ser Arg Thr Pro
                20                  25                  30
Glu Val Thr Cys Val Val Val Asp Val Ser His Glu Asp Pro Glu Val
                35                  40                  45
Lys Phe Asn Trp Tyr Val Asp Gly Val Glu Val His Asn Ala Lys Thr
                50                  55                  60
Lys Pro Arg Glu Glu Gln Tyr Asn Ser Thr Tyr Arg Val Val Ser Val
65                  70                  75                  80
Leu Thr Val Leu Ala Gln Asp Trp Leu Asn Gly Lys Glu Tyr Lys Cys
                85                  90                  95
Lys Val Ser Asn Lys Ala Leu Pro Ala Pro Ile Glu Lys Thr Ile Ser
                100                 105                 110
Lys Ala Lys Gly Gln Pro Arg Glu Pro Gln Val Tyr Thr Leu Pro Pro
                115                 120                 125
Ser Arg Asp Glu Leu Thr Lys Asn Gln Val Ser Leu Thr Cys Leu Val
                130                 135                 140
Lys Gly Phe Tyr Pro Ser Asp Ile Ala Val Glu Trp Glu Ser Asn Gly
145                 150                 155                 160
Gln Pro Glu Asn Asn Tyr Lys Thr Thr Pro Pro Val Leu Asp Ser Asp
                165                 170                 175
Gly Ser Phe Phe Leu Tyr Ser Lys Leu Thr Val Asp Lys Ser Arg Trp
                180                 185                 190
Gln Gln Gly Asn Val Phe Ser Cys Ser Val Met His Glu Ala Leu His
                195                 200                 205
Asn Ala Tyr Thr Gln Lys Ser Leu Ser Leu Ser Pro Gly
                210                 215                 220

<210> SEQ ID NO 20
<211> LENGTH: 221
<212> TYPE: PRT
<213> ORGANISM: Artificial Sequence
<220> FEATURE:
<223> OTHER INFORMATION: variant human Fc-region of the IgG1 subclass
      with the mutations H310A, H433A and Y436A

<400> SEQUENCE: 20

Cys Pro Pro Cys Pro Ala Pro Glu Leu Leu Gly Gly Pro Ser Val Phe
```

```
                1               5                   10                  15
Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
                50                  55                  60

Lys Pro Arg Glu Glu Gln Tyr Asn Ser Thr Tyr Arg Val Val Ser Val
65                  70                  75                  80

Leu Thr Val Leu Ala Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Arg Asp Glu Leu Thr Lys Asn Gln Val Ser Leu Thr Cys Leu Val
                130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu Ala
                195                 200                 205

Asn His Ala Thr Gln Lys Ser Leu Ser Leu Ser Pro Gly
                210                 215                 220

<210> SEQ ID NO 21
<211> LENGTH: 221
<212> TYPE: PRT
<213> ORGANISM: Artificial Sequence
<220> FEATURE:
<223> OTHER INFORMATION: variant human Fc-region of the IgG1 subclass
      with the mutations M252Y, S254T and T256E

<400> SEQUENCE: 21

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Tyr Ile Thr Arg Glu Pro
                20                  25                  30

Glu Val Thr Cys Val Val Val Asp Val Ser His Glu Asp Pro Glu Val
                35                  40                  45

Lys Phe Asn Trp Tyr Val Asp Gly Val Glu Val His Asn Ala Lys Thr
                50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
                115                 120                 125

Ser Arg Asp Glu Leu Thr Lys Asn Gln Val Ser Leu Thr Cys Leu Val
                130                 135                 140
```

```
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220
```

<210> SEQ ID NO 22
<211> LENGTH: 228
<212> TYPE: PRT
<213> ORGANISM: Homo sapiens

<400> SEQUENCE: 22

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

<210> SEQ ID NO 23
<211> LENGTH: 228
<212> TYPE: PRT
<213> ORGANISM: Artificial Sequence
<220> FEATURE:
<223> OTHER INFORMATION: variant human Fc-region of the IgG4 isotype
      with a S228P and L235E mutation

<400> SEQUENCE: 23

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly
225

<210> SEQ ID NO 24
<211> LENGTH: 228
<212> TYPE: PRT
<213> ORGANISM: Artificial Sequence
<220> FEATURE:
<223> OTHER INFORMATION: variant human Fc-region of the IgG4 isotype
      with a S228P, L235E and P329G mutation

<400> SEQUENCE: 24

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
            115                 120                 125
```

```
Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 25
<211> LENGTH: 228
<212> TYPE: PRT
<213> ORGANISM: Artificial Sequence
<220> FEATURE:
<223> OTHER INFORMATION: variant human Fc-region of the IgG4 isotype
      with a S228P and L235E mutation

<400> SEQUENCE: 25

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

```
<210> SEQ ID NO 26
<211> LENGTH: 228
<212> TYPE: PRT
<213> ORGANISM: Artificial Sequence
<220> FEATURE:
<223> OTHER INFORMATION: variant human Fc-region of the IgG4 isotype
      with a S228P, L235E and P329G mutation

<400> SEQUENCE: 26
```

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly
225

```
<210> SEQ ID NO 27
<211> LENGTH: 107
<212> TYPE: PRT
<213> ORGANISM: Homo sapiens

<400> SEQUENCE: 27
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser

```
                    85                  90                  95
Pro Val Thr Lys Ser Phe Asn Arg Gly Glu Cys
                100                 105

<210> SEQ ID NO 28
<211> LENGTH: 105
<212> TYPE: PRT
<213> ORGANISM: Homo sapiens

<400> SEQUENCE: 28

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105
```